United States Patent [19]
Axworthy et al.

[11] Patent Number: 5,914,312
[45] Date of Patent: Jun. 22, 1999

[54] PRETARGETING METHODS AND COMPOUNDS

[75] Inventors: Donald B. Axworthy, Brier; Alan R. Fritzberg, Edmonds; James A. Sanderson, Seattle, all of Wash.

[73] Assignee: NeoRx Corporation, Seattle, Wash.

[21] Appl. No.: 08/297,429

[22] Filed: Aug. 26, 1994

Related U.S. Application Data

[63] Continuation of application No. 07/995,383, Dec. 23, 1992, abandoned, which is a continuation-in-part of application No. 07/895,588, Jun. 9, 1992, Pat. No. 5,283,342.

[51] Int. Cl.$^6$ .................. C07K 14/435; C07K 14/47; C07D 257/02
[52] U.S. Cl. ................ 514/8; 514/387; 530/363; 530/367; 530/350; 530/395; 530/394; 568/852; 536/112; 548/303.7
[58] Field of Search ............................ 536/112; 514/387, 514/8; 548/303.7; 530/363, 367, 387.1, 391.1, 350, 395, 394; 568/852; 525/329.5

[56] References Cited

U.S. PATENT DOCUMENTS 4,863,713   9/1989   Goodwin et al. ................ 424/1.1

FOREIGN PATENT DOCUMENTS

| | | |
|---|---|---|
| 0 251 494 | 1/1988 | European Pat. Off. . |
| 0 496 074 | 7/1992 | European Pat. Off. . |
| PCT/DE88/00200 | 11/1988 | Germany . |
| 89/10140 | 11/1989 | WIPO . |

OTHER PUBLICATIONS

Sharkey, R.M. et al., Radiobiology/Radiation Oncology #4192, American Association for Cancer Research, vol. 37, Mar. 1996, p. 611.
Robert W. Thornburg et al., Carbohydrate–mediated Clearance of Immune Complexes from the Circulation—A Role for Galactose Residues in the Hepatic Uptake of IgG–Antigen Complexes, The Journal of Biological Chemistry, vol. 255, No. 14, Jul. 25, 1980, pp. 6820–6825.
Harris et al., Tibtech 11:42, 1993, Therapeutic . . . Age.
Hird et al., Cancer & Genes, 1990, Immunotherapy . . . Antibodies.
Wileman et al., 1986, J. Pharm. Pharmacol., 38: 264, Soluble . . . Reactivity Sigma Catalog, 1989, p. 104.
Kindt et al., The Antibody Enigma, pp. 71–72, 1984.
Kuchler et al., Eur. J. Cell. Bio., 1990, 52(1):87–97.
Galli et al., J. Nucl. Med. Allied Sci., 1988, 32(2):110.
Morrell et al., J. Biol. Chem., 1971, 246(5):1461.
Mattes, 1987, JNCI, 79(4):855.
Vansteenkiste et al., J. Controlled Release, 1991, 16:91.
Sharma, S.K. et al., "Inactivation and clearance of an anti–CEA carboxypeptidase G2 conjugate in blood after localisation in a xenograft model." Br. J. Cancer (1990), 61, 659–662.
Goodwin et al., *J. Nucl. Med.*, vol. 33, No. 11, pp. 2006–2013, "Pretargeted Immunoscintigraphy: Effect of Hapten Valency on Murine Tumor Uptake".

Morell et al., *J. Biol. Chem.*, vol. 246, No. 1, p. 1461–1467, "The Role of Sialic Acid in Determining the Survival of Glycoproteins in the Circulation".
Tolleshaug, *Int. J. Biochem.*, vol. 13, pp. 45–51, "Binding and Internalization of Asialo–glycoproteins by Isolated Rat Hepatocytes".
Wall et al., *Cell*, vol. 21, pp. 79–93, "The Galactose–Specific Recognition System of Mammalian Liver: The Route of Ligand Internalization in Rat Hepatocytes".
Galli et al., *J. Nucl. Med.*, vol. 32, No. 2, pp. 110–116, "A Radio–pharmaceutical for the Study of the Liver:$^{99m}$Tc–DTPA–Asialo–Orosomucoid I: Radiochemical and Animal Distribution Studies".
Van Der Sluijs et al.,*Hepatology*, vol. 6, No. 4, pp. 723–728, 1986, "Drug Targeting to the liver with lactosylated albumins: does the glycoprotein target the drug or is the drug targeting the glycoprotein?".
Virzi et al., *Nucl. Med. Biol.*, vol. 18, No. 7, pp. 719–726, 1991, "New Indium–111 Labeled Biotin Derivates for Improved Immunortargeting".
R. T. Lee et al, *Glycoconjugate*, "Preparation of Cluster Glycosides of N–Acetylgalactosamine That Have Subnanomolar Binding Constants Towards the Mammalian Hepatic Gal/GalNAc–specific Receptor", vol. 4, (1987), pp. 317–328.
R. T. Lee et al, *Biochemistry*, "New Synthetic Cluster Ligands for Galactose/N–Acetylgalactosamine–Specific Lectin of Mammalian Liver", vol. 23, (1984), pp. 4255–4261.
J. R. Merwin et al, *Bioconjugate Chem.*, "Targeted Delivery of DNA Using YEE(GalNAcAH)$_3$, a Synthetic Glycopeptide Ligand for the Asialoglycoprotein Receptor", vol. 5 (1994), pp. 612–620.
M. A. Findeis, *Int. J. Peptide Protein Res.*, "Stepwise synthesis of a GalNAc–containing cluster glycoside ligand of the asialoglycoprotein receptor", vol. 43, (1994), pp. 477–485.
T. D. McKee et al, *Bioconjugate Chem.*, "Preparation of Asialoorosomucoid–Polylysine Conjugates", vol. 5, (1994), pp. 306–311.
E. A. L. Biessen et al, *J. Med. Chem.*, "Synthesis of Cluster Galactosides with High Affinity for the Hepatic Asialoglycoprotein Receptor", vol. 83 No. 9, (1995), pp. 1538–1546.

(List continued on next page.)

*Primary Examiner*—Frank C. Eisenschenk
*Assistant Examiner*—Patrick Nolan
*Attorney, Agent, or Firm*—Seed and Berry LLP

[57] ABSTRACT

Methods, compounds, compositions and kits that relate to pretargeted delivery of diagnostic and therapeutic agents are disclosed. In particular, methods for radiometal labeling of biotin and for improved radiohalogenation of biotin, as well as related compounds, are described. Also, clearing agents, anti-ligand-targeting moiety conjugates, target cell retention enhancing moieties and additional methods are discussed.

5 Claims, 22 Drawing Sheets

OTHER PUBLICATIONS

Sheldon et al., *Appl. Radiat. Isot.,* vol. 43, pp. 1399–1402, "Targeting of [$^{111}$In]Biocytin to Cultured Ovarian Adenocarcinoma Cells Using Covalent Monoclonal Antibody–Streptavidin Conjugates".

Sharon et al., *Scientific American,* vol. 268, No. 1, pp. 82–89, "Carbohydrates in Cell Recognition".

Goodwin, *J. Nucl. Med.,* vol. 33, No. 10, pp. 1816–1818, "New Methods for Localizing Infection: A role for Avidn–Biotin?".

| | +PBS | SD | +NON-BT | SD | +10:1 | SD | +5:1 | SD | BT-SAT'D | SD |
|---|---|---|---|---|---|---|---|---|---|---|
| BLOOD | 31.05 | 5.08 | 29.94 | 1.35 | 8.54 | 0.91 | 7.03 | 0.18 | 24.58 | 0.68 |
| TAIL | 2.43 | 0.70 | 1.80 | 0.09 | 1.46 | 0.09 | 1.76 | 0.04 | 1.96 | 0.40 |
| LUNG | 1.47 | 0.26 | 1.09 | 0.22 | 0.54 | 0.10 | 0.48 | 0.07 | 0.76 | 0.01 |
| LIVER | 5.42 | 0.69 | 4.66 | 0.36 | 9.60 | 1.20 | 9.11 | 0.41 | 6.76 | 0.06 |
| SPLEEN | 0.25 | 0.05 | 0.34 | 0.03 | 0.17 | 0.03 | 0.18 | 0.00 | 0.38 | 0.02 |
| STOMACH | 0.28 | 0.02 | 0.33 | 0.03 | 0.53 | 0.34 | 0.49 | 0.00 | 0.29 | 0.04 |
| KIDNEY | 1.72 | 0.24 | 1.38 | 0.08 | 2.76 | 0.00 | 3.28 | 0.32 | 1.58 | 0.08 |
| INTESTINE | 3.40 | 0.73 | 3.44 | 0.10 | 4.22 | 0.02 | 6.62 | 0.14 | 2.83 | 0.13 |
| | 46.02 | | 42.98 | | 27.83 | | 28.95 | | 39.13 | |
| | Group 1 | | Group 2 | | Group 3 | | Group 4 | | Group 5 | |

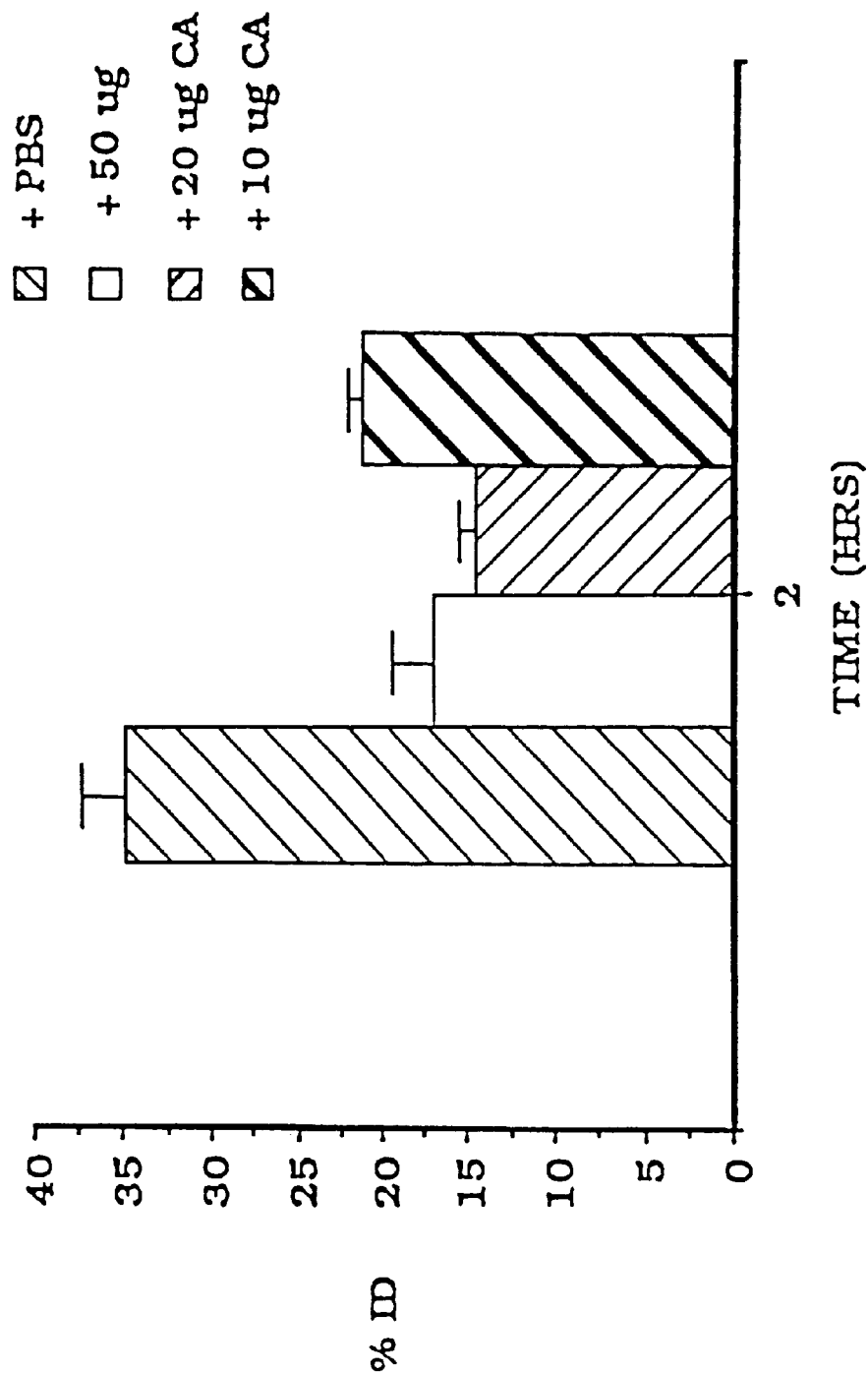

5,914,312

PRETARGETING METHODS AND COMPOUNDS

CROSS-REFERENCE TO RELATED APPLICATIONS

This application is a continuation of prior application Ser. No. 07/995,383, filed Dec. 23, 1992 now abandoned, which is a continuation in part of Ser. No. 07/895,588, filed Jun. 9, 1992, now U.S. Pat. No. 5,283,342.

TECHNICAL FIELD

The present invention relates to methods, compounds, compositions and kits useful for delivering to a target site a targeting moiety that is conjugated to one member of a ligand/anti-ligand pair. After localization and clearance of the targeting moiety conjugate, direct or indirect binding of a diagnostic or therapeutic agent conjugate at the target site occurs. Methods for radiometal labeling of biotin and for improved radiohalogenation of biotin, as well as the related compounds, are also disclosed. Also, clearing agents, anti-ligand targeting moiety conjugates, target cell-retention enhancing moieties and additional methods are set forth.

BACKGROUND OF THE INVENTION

Conventional cancer therapy is plagued by two problems. The generally attainable targeting ratio (ratio of administered dose localizing to tumor versus administered dose circulating in blood or ratio of administered dose localizing to tumor versus administered dose migrating to bone marrow) is low. Also, the absolute dose of radiation or therapeutic agent delivered to the tumor is insufficient in many cases to elicit a significant tumor response. Improvement in targeting ratio or absolute dose to tumor is sought.

SUMMARY OF THE INVENTION

The present invention is directed to diagnostic and therapeutic pretargeting methods, moieties useful therein and methods of making those moieties. Such pretargeting methods are characterized by an improved targeting ratio or increased absolute dose to the target cell sites in comparison to conventional cancer therapy.

The present invention describes chelate-biotin compounds and radiohalogenated biotin compounds useful in diagnostic and therapeutic pretargeting methods. The present invention also provides targeting moiety-ligand, such as biotin, compounds useful in diagnostic and therapeutic pretargeting methods. Selection of moieties and methodologies used to enhance internalization (of chemotherapeutic drugs, for example) or to enhance retention at the target cell surface (of radionuclides, for example) is also discussed.

In addition, the present invention provides targeting moiety-anti-ligand, such as avidin or streptavidin, compounds useful in diagnostic and therapeutic pretargeting methods. Preparation and purification of such anti-ligand-targeting moiety compounds are also discussed.

The present invention also provides clearing agents to facilitate the removal of circulating targeting moiety-ligand (two-step) or targeting moiety-anti-ligand (two-step) or anti-ligand (three-step) from the mammalian recipient. Preferred clearing agents are classifiable as galactose-based and non-galactose-based. Within each category, preferable clearing agents are polymeric or protein based.

Also, the present invention is directed to methods using streptavidin as an anti-ligand to enhance retention of radionuclide at target cell sites, with pretargeting protocols constituting one such method. More specifically, these embodiments of the present invention involve either (1) targeting moiety-streptavidin-radionuclide (with the radionuclide bound to streptavidin directly or through a chelate or linker), as well as (2) targeting moiety-biotin administered prior to streptavidin-radionuclide, or (3) biotin-radionuclide bound to a pretargeted streptavidin containing molecule.

The present invention further provides pretargeting methods employing intraarterial administration of the therapeutic moiety-containing molecule to achieve greater localization thereof to artery-supplied target cell populations. Other methods of the present invention involve lo administration of short duration bone marrow protecting agents-prior to radionuclide-ligand molecule or radionuclide-anti-ligand molecule administration. Further, monovalent targeting moieties, such as Fv or Fab antibody fragments, are useful in the inventive pretargeting methods. Delivery of other, non-radioactive therapeutic agents, such as chemotherapeutic drugs, anti-tumor agents (e.g., cytokines) and toxins, to target cells using the pretargeting methods of the present invention is also described.

BRIEF DESCRIPTION OF THE DRAWINGS

FIG. 8 shows limited biodistribution data for LU-10-StrAv conjugate upon administration of three controls (Groups 1, 2 and 5) and two doses of clearing agent (Groups 3 and 4) at two hours post-clearing agent administration.

FIG. 11A depicts the blood clearance of LU-10-StrAv conjugate upon administration of a control (PBS) and three doses (50, 20 and 10 μg) of clearing agent at two hours post-clearing agent administration.

DETAILED DESCRIPTION OF THE INVENTION

Figure 1:
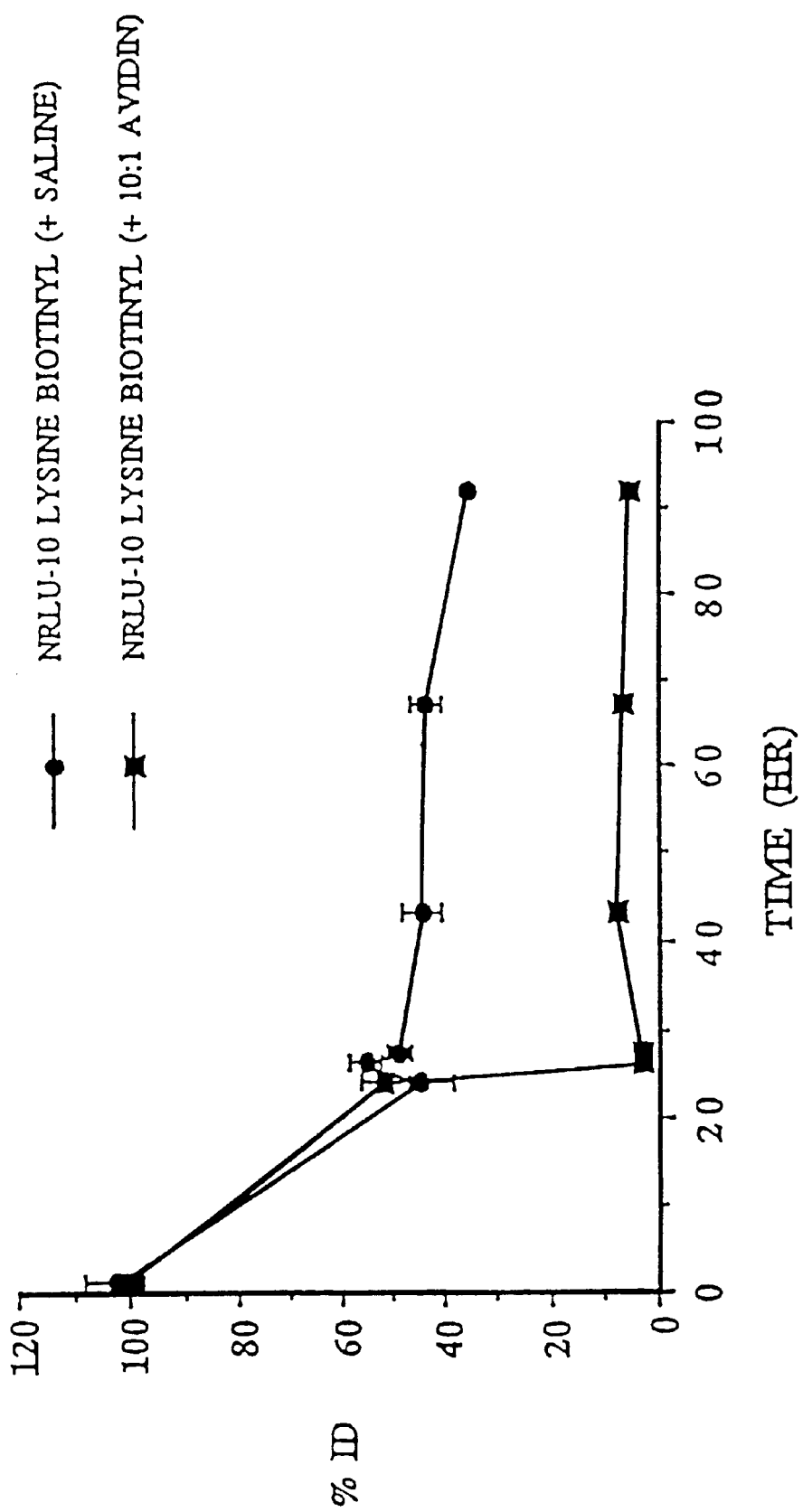
FIG. 1 illustrates blood clearance of biotinylated antibody following intravenous administration of avidin.

Prior to setting forth the invention, it may be helpful to set forth definitions of certain terms to be used within the disclosure.

Targeting moiety: A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include hapten/antibody, lectin/carbohydrate, ligand/receptor, and biotin/avidin. Biotin/avidin is used throughout the specification as a prototypical example of a ligand/anti-ligand pair.

Anti-ligand: As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Anti-ligands of the present invention may exhibit or be derivitized to exhibit structural features that direct the uptake thereof, e.g., galactose residues that direct liver uptake. Avidin and streptavidin are used herein as prototypical anti-ligands.

Avidin: As defined herein, "avidin" includes avidin, streptavidin and derivatives and analogs thereof that are capable of high affinity, multivalent or univalent binding of biotin.

Ligand: As defined herein, a "ligand" is a relatively small, soluble molecule that exhibits rapid serum, blood and/or whole body clearance when administered intravenously in an animal or human. Biotin is used as the prototypical ligand.

Active Agent: A diagnostic or therapeutic agent ("the payload"), including radionuclides, drugs, anti-tumor agents, toxins and the like. Radionuclide therapeutic agents are used as prototypical active agents.

$N_xS_y$ Chelates: As defined herein, the term "$N_xS_y$ chelates" includes bifunctional chelators that are capable of (i) coordinately binding a metal or radiometal and (ii) covalently attaching to a targeting moiety, ligand or anti-ligand. Particularly preferred $N_xS_y$ chelates have $N_2S_2$ and $N_3S$ cores. Exemplary $N_xS_y$ chelates are described in Fritzberg et al., *Proc. Natl. Acad. Sci. USA* 85:4024–29, 1988; in Weber et al., *Bioconj. Chem.* 1:431–37, 1990; and in the references cited therein, for instance.

Pretargeting: As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site. Three-step and other related methods described herein are also encompassed.

Clearing Agent: An agent capable of binding, complexing or otherwise associating with an administered moiety (e.g., targeting moiety-ligand, targeting moiety-anti-ligand or anti-ligand alone) present in the recipient's circulation, thereby facilitating circulating moiety clearance from the recipient's body, removal from blood circulation, or inactivation thereof in circulation. The clearing agent is preferably characterized by physical properties, such as size, charge, configuration or a combination thereof, that limit clearing agent access to the population of target cells recognized by a targeting moiety used in the same treatment protocol as the clearing agent.

Target Cell Retention: The amount of time that a radionuclide or other therapeutic agent remains at the target cell surface or within the target cell. Catabolism of conjugates or molecules containing such therapeutic agents appears to be primarily responsible for the loss of target cell retention.

A recognized disadvantage associated with in vivo administration of targeting moiety-radioisotopic conjugates for imaging or therapy is localization of the attached radioactive agent at both non-target and target sites. Until the administered radiolabeled conjugate clears from the circulation, normal organs and tissues are transitorily exposed to the attached radioactive agent. For instance, radiolabeled whole antibodies that are administered in vivo exhibit relatively slow blood clearance; maximum target site localization generally occurs 1–3 days post-administration. Generally, the longer the clearance time of the conjugate from the circulation, the greater the radioexposure of non-target organs.

These characteristics are particularly problematic with human radioimmunotherapy. In human clinical trials, the long circulating half-life of radioisotope bound to whole antibody causes relatively large doses of radiation to be delivered to the whole body. In particular, the bone marrow, which is very radiosensitive; is the dose-limiting organ of non-specific toxicity.

In order to decrease radioisotope exposure of non-target tissue, potential targeting moieties generally have been screened to identify those that display minimal non-target reactivity, while retaining target specificity and reactivity. By reducing non-target exposure (and adverse non-target localization and/or toxicity) increased doses of a radiotherapeutic conjugate may be administered; moreover, decreased non-target accumulation of a radiodiagnostic conjugate leads to improved contrast between background and target.

Therapeutic drugs, administered alone or as targeted conjugates, are accompanied by similar disadvantages. Again, the goal is administration of the highest possible concentration of drug (to maximize exposure of target tissue), while remaining below the threshold of unacceptable normal organ toxicity (due to non-target tissue exposure). Unlike radioisotopes, however, therapeutic drugs need to be taken into a target cell to exert a cytotoxic effect. In the case of targeting moiety-therapeutic drug conjugates, it would be advantageous to combine the relative target specificity of a targeting moiety with a means for enhanced target cell internalization of the targeting moiety-drug conjugate.

In contrast, enhanced target cell internalization is disadvantageous if one administers diagnostic agent-targeting moiety conjugates. Internalization of diagnostic conjugates results in cellular catabolism and degradation of the conjugate. Upon degradation, small adducts of the diagnostic agent or the diagnostic agent per se may be released from the cell, thus eliminating the ability to detect the conjugate in a target-specific manner.

One method for reducing non-target tissue exposure to a diagnostic or therapeutic agent involves "pretargeting" the targeting moiety at a target site, and then subsequently administering a rapidly clearing diagnostic or therapeutic agent conjugate that is capable of binding to the "pretargeted" targeting moiety at the target site. A description of some embodiments of the pretargeting technique may be found in U.S. Pat. No. 4,863,713 (Goodwin et al.).

A typical pretargeting approach ("three-step") is schematically depicted below.

Briefly, this three-step pretargeting protocol features administration of an antibody-ligand conjugate, which is allowed to localize at a target site and to dilute in the circulation. Subsequently administered anti-ligand binds to the antibody-ligand conjugate and clears unbound antibody-ligand conjugate from the blood. Preferred anti-ligands are large and contain sufficient multivalency to accomplish crosslinking and aggregation of circulating antibody-ligand conjugates. The clearing by anti-ligand is probably attributable to anti-ligand crosslinking and/or aggregation of antibody-ligand conjugates that are circulating in the blood, which leads to complex/aggregate clearance by the recipient's RES (reticuloendothelial system). Anti-ligand clearance of this type is preferably accomplished with a multi-valent molecule; however, a univalent molecule of sufficient size to be cleared by the RES on its own could also be employed. Alternatively, receptor-based clearance mechanisms, e.g., Ashwell receptor galactose residue recognition mechanisms, may be responsible for anti-ligand clearance. Such clearance mechanisms are less dependent upon the valency of the anti-ligand with respect to the ligand than the RES complex/aggregate clearance mechanisms. It

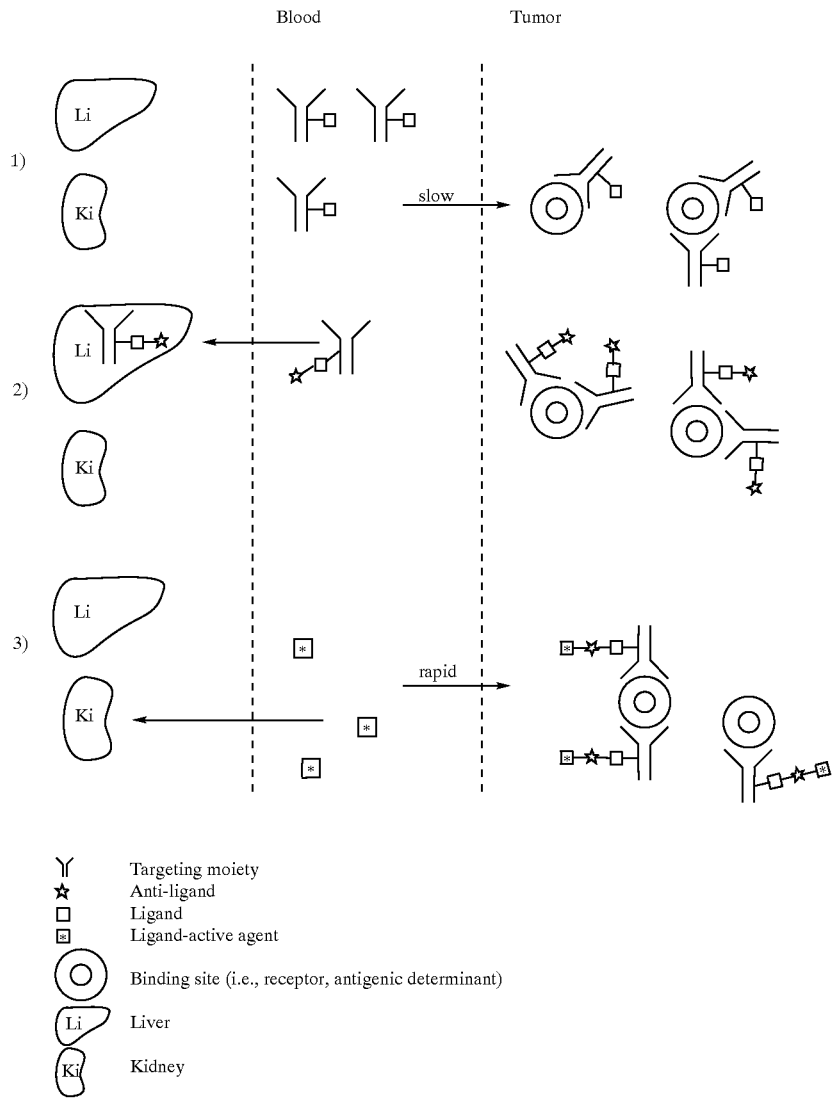

is preferred that the ligand-anti-ligand pair displays relatively high affinity binding.

A diagnostic or therapeutic agent-ligand conjugate that exhibits rapid whole body clearance is then administered. When the circulation brings the active agent-ligand conjugate in proximity to the target cell-bound antibody-ligand-anti-ligand complex, anti-ligand binds the circulating active agent-ligand conjugate and produces an antibody-ligand:anti-ligand:ligand-active agent "sandwich" at the target site. Because the diagnostic or therapeutic agent is attached to a rapidly clearing ligand (rather than antibody, antibody fragment or other slowly clearing targeting moiety), this technique promises decreased non-target exposure to the active agent.

Alternate pretargeting methods eliminate the step of parenterally administering an anti-ligand clearing agent. These "two-step" procedures feature targeting moiety-ligand or targeting moiety-anti-ligand administration, followed by administration of active agent conjugated to the opposite member of the ligand-anti-ligand pair. As an optional step "1.5" in the two-step pretargeting methods of the present invention, a clearing agent (preferably other than ligand or anti-ligand) is administered to facilitate the clearance of circulating targeting moiety-containing conjugate.

In the two-step pretargeting approach, the clearing agent preferably does not become bound to the target cell population, either directly or through the previously administered and target cell bound targeting moiety-anti-ligand or targeting moiety-ligand conjugate. An example of two-step pretargeting involves the use of biotinylated human transferrin as a clearing agent for avidin-targeting moiety conjugate, wherein the size of the clearing agent results in liver clearance of transferrin-biotin-circulating avidin-targeting moiety complexes and substantially precludes association with the avidin-targeting moiety conjugates bound at target cell sites. (See, Goodwin, D. A., *Antibod. Immunoconj. Radiopharm.*, 4: 427–34, 1991).

The two-step pretargeting approach overcomes certain disadvantages associated with the use of a clearing agent in a three-step pretargeted protocol. More specifically, data obtained in animal models demonstrate that in vivo anti-ligand binding to a pretargeted targeting moiety-ligand conjugate (i.e., the cell-bound conjugate) removes the targeting moiety-ligand conjugate from the target cell. One explanation for the observed phenomenon is that the multivalent anti-ligand crosslinks targeting moiety-ligand conjugates on the cell surface, thereby initiating or facilitating internalization of the resultant complex. The apparent loss of targeting moiety-ligand from the cell might result from internal degradation of the conjugate and/or release of active agent from the conjugate (either at the cell surface or intracellularly). An alternative explanation for the observed phenomenon is that permeability changes in the target cell's membrane allow increased passive diffusion of any molecule into the target cell. Also, some loss of targeting moiety-ligand may result from alteration in the affinity by subsequent binding of another moiety to the targeting moiety-ligand, e.g., anti-idiotype monoclonal antibody binding causes removal of tumor bound monoclonal antibody.

The present invention recognizes that this phenomenon (apparent loss of the targeting moiety-ligand from the target cell) may be used to advantage with regard to in vivo delivery of therapeutic agents generally, or to drug delivery in particular. For instance, a targeting moiety may be covalently linked to both ligand and therapeutic agent and administered to a recipient. Subsequent administration of anti-ligand crosslinks targeting moiety-ligand-therapeutic agent tripartite conjugates bound at the surface, inducing internalization of the tripartite conjugate (and thus the active agent). Alternatively, targeting moiety-ligand may be delivered to the target cell surface, followed by administration of anti-ligand-therapeutic agent.

In one aspect of the present invention, a targeting moiety-anti-ligand conjugate is administered in vivo; upon target localization of the targeting moiety-anti-ligand conjugate (i.e., and clearance of this conjugate from the circulation), an active agent-ligand conjugate is parenterally administered. This method enhances retention of the targeting moiety-anti-ligand:ligand-active agent complex at the target cell (as compared with targeting moiety-ligand:anti-ligand:ligand-active agent complexes and targeting moiety-ligand:anti-ligand-active agent complexes). Although a variety of ligand/anti-ligand pairs may be suitable for use within the claimed invention, a preferred ligand/anti-ligand pair is biotin/avidin.

In a second aspect of the invention, radioiodinated biotin and related methods are disclosed. Previously, radioiodinated biotin derivatives were of high molecular weight and were difficult to characterize. The radioiodinated biotin described herein is a low molecular weight compound that has been easily and well characterized.

In a third aspect of the invention, a targeting moiety-ligand conjugate is administered in vivo; upon target localization of the targeting moiety-ligand conjugate (i.e., and clearance of this conjugate from the circulation), a drug-anti-ligand conjugate is parenterally administered. This two-step method not only provides pretargeting of the targeting moiety conjugate, but also induces internalization of the subsequent targeting moiety-ligand-anti-ligand-drug complex within the target cell. Alternatively, another embodiment provides a three-step protocol that produces a targeting moiety-ligand:anti-ligand:ligand-drug complex at the surface, wherein the ligand-drug conjugate is administered simultaneously or within a short period of time after administration of anti-ligand (i.e., before the targeting moiety-ligand-anti-ligand complex has been removed from the target cell surface).

In a fourth aspect of the invention, methods for radiolabeling biotin with technetium-99m, rhenium-186 and rhenium-188 are disclosed. Previously, biotin derivatives were radiolabeled with indium-111 for use in pretargeted immunoscintigraphy (for instance, Virzi et al., *Nucl. Med. Biol.* 18:719–26, 1991; Kalofonos et al., *J. Nucl. Med.* 31: 1791–96, 1990; Paganelli et al. *Canc. Res.* 51:5960–66, 1991). However, $^{99m}$Tc is a particularly preferred radionuclide for immunoscintigraphy due to (i) low cost, (ii) convenient supply and (iii) favorable nuclear properties. Rhenium-186 displays chelating chemistry very similar to $^{99m}$Tc, and is considered to be an excellent therapeutic radionuclide (i.e., a 3.7 day half-life and 1.07 MeV maximum particle that is similar to $^{131}$I). Therefore, the claimed methods for technetium and rhenium radiolabeling of biotin provide numerous advantages.

The "targeting moiety" of the present invention binds to a defined target cell population, such as tumor cells. Preferred targeting moieties useful in this regard include antibody and antibody fragments, peptides, and hormones. Proteins corresponding to known cell surface receptors (including low density lipoproteins; transferrin and insulin), fibrinolytic enzymes, anti-HER2, and biological response modifiers (including interleukin, interferon, erythropoietin and colony-stimulating factor) are also preferred targeting moieties. Also, anti-EGF receptor antibodies, which internalize following binding to the receptor and traffic to the nucleus to an extent, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.*, 20: 284–6, 1956), affinity-purified polyclonal or fragments thereof (Chao et al., *Res. Comm. in Chem. Path. & Pharm.*, 9: 749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature*, 256: 495–97, 1975, *Eur. J. Immunol.*, 6: 511–19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Humanized targeting moieties are recognized to decrease the immunoreactivity of the antibody or polypeptide in the host recipient, permitting an increase in the half-life and a reduction in the possibility of adverse immune reactions.

Types of active agents (diagnostic or therapeutic) useful herein include toxins, anti-tumor agents, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

Preferred toxins in this regard include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein.

Preferred drugs suitable for use herein include conventional chemotherapeutics, such as vinblastine, doxorubicine bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A particularly preferred drug within the present invention is a trichothecene.

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone; flavone-8-acetic acid, oxantrazole, ipomeanol, trimetrexate, deoxyspergualin, echinomycin, and dideoxycytidine (see *NCI Investigational Drugs, Pharmaceutical Data* 1987, NIH Publication No. 88-2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}I$, $^{125}I$, $^{130}I$, $^{131}I$, $^{133}I$, $^{135}I$, $^{47}SC$, $^{72}As$, $^{72}Se$, $^{90}Y$, $^{97}Ru$, $^{100}Pd$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Ga$, $^{68}Ga$, $^{67}Cu$, $^{75}Br$, $^{76}Br$, $^{77}Br$, $^{99m}Tc$, $^{11}C$, $^{13}N$, $^{15}O$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$ or $^{177}Lu$.

Other anti-tumor agents are administrable in accordance with the present invention. Exemplary anti-tumor agents include cytokines, such as IL-2, tumor necrosis factor or the like, lectin inflammatory response promoters (selecting), such as L-selectin, E-selectin, P-selectin or the like, and like molecules.

Ligands suitable for use within the present invention include biotin, haptens, lectins, epitopes and analogs and derivatives thereof. Useful complementary anti-ligands include avidin (for biotin), carbohydrates (for lectins) and antibody, fragments or analogs thereof, including mimetics (for haptens and epitopes). Preferred ligands and anti-ligands bind to each other with an affinity of at least about $k_D \geq 10^9$ M.

One component to be administered in a preferred two-step pretargeting protocol is a targeting moiety-avidin or a targeting moiety-streptavidin conjugate. The preferred targeting moiety useful in these embodiments of the present invention is a monoclonal antibody. Protein-protein conjugations are generally problematic due to the formation of undesirable byproducts, including high molecular weight and cross linked species, however. A non-covalent synthesis technique involving reaction of biotinylated antibody with streptavidin has been reported to result in substantial byproduct formation. Also, at least one of the four biotin binding sites on the streptavidin is used to link the antibody and streptavidin, while another such binding site may be sterically unavailable for biotin binding due to the configuration of the streptavidin-antibody conjugate.

Thus, covalent streptavidin-antibody conjugation is preferred, but high molecular weight byproducts are often obtained. The degree of crosslinking and aggregate formation is dependent upon several factors, including the level of protein derivitization using heterobifunctional crosslinking reagents. Sheldon et al., *Appl. Radiat. Isot.* 43: 1399–1402, 1992, discuss preparation of covalent thioether conjugates by reacting succinimidyl 4-(N-maleimidomethyl) cyclohexane-1-carboxylate (SMCC)derivitized antibody and iminothiolane-derivitized streptavidin.

Streptavidin-proteinaceous targeting moiety conjugates are preferably prepared as described in Example XI below, with the preparation involving the steps of: preparation of SMCC-derivitized streptavidin; preparation of DTT-reduced proteinaceous targeting moiety; conjugation of the two prepared moieties; and purification of the monosubstituted conjugate. The purified fraction is preferably further characterized by one or more of the following techniques: HPLC size exclusion, SDS-PAGE, immunoreactivity, biotin binding capacity and in vivo studies.

Alternatively, thioether conjugates useful in the practice of the present invention may be formed using other thiolating agents, such as SPDP, iminothiolate, SATA or the like, or other thio-reactive heterobifunctional cross linkers, such as m-maleimidobenzoyl-N-hydroxysuccinimide ester, N-succinimidyl(4-iodoacetyl)aminobenzoate or the like.

Streptavidin-proteinaceous targeting moiety conjugates of the present invention can also be formed by conjugation of a lysine epsilon amino group of one protein with a maleimide-derivitized form of the other protein. For example, at pH 8–10, lysine epsilon amino moieties react with protein maleimides, prepared, for instances by treatment of the protein with SMCC, to generate stable amine covalent conjugates. In addition, conjugates can be prepared by reaction of lysine epsilon amino moieties of one protein with aldehyde functionalities of the other protein. The resultant imine bond is reducible to generate the corresponding stable amine bond. Aldehyde functionalities may be generated, for example, by oxidation of protein sugar residues or by reaction with aldehyde-containing heterobifunctional cross linkers.

Another method of forming streptavidin-targeting moiety conjugates involves immobilized iminobiotin that binds SMCC-derivitized streptavidin. In this conjugation/purification method, the reversible binding character of iminobiotin (immobilized) to streptavidin is exploited to readily separate conjugate from the unreacted targeting moiety. Iminobiotin binding can be reversed under conditions of lower pH and elevated ionic strength, e.g., NH$_2$OAc, pH 4 (50 mM) with 0.5 M NaCl.

For streptavidin, for example, the conjugation/purification proceeds as follows:

SMCC-derivitized streptavidin is bound to immobilized iminobiotin (Pierce Chemical Co., St. Louis, Mo.), preferably in column format;

a molar excess (with respect to streptavidin) of DTT-reduced antibody (preferably free of reductant) is added to the nitrogen-purged, phosphate-buffered iminobiotin column wherein the SMCC-streptavidin is bound (DTT-reduced antibody will saturate the bound SMCC-streptavidin, and unbound reduced antibody passing through the column can be reused);

the column is washed free of excess antibody; and a buffer that lowers the pH and increases ionic strength is added to the column to elute streptavidin-antibody conjugate in pure form.

As indicated above, targeting moiety-mediated ligand-anti-ligand pretargeting involves the localization of either targeting moiety-ligand or targeting moiety-anti-ligand at target tissue. Often, peak uptake to such target tissue is achieved before the circulating level of targeting moiety-containing conjugate in the blood is sufficiently low to permit the attainment of an optimal target-to-non-target conjugate ratio. To obviate this problem, two approaches are useful. The first approach allows the targeting moiety-containing conjugate to clear from the blood by "natural" or endogenous clearance mechanisms. This method is complicated by variations in systemic clearance of-proteins and by endogenous ligand or anti-ligand. For example, endogenous biotin may interfere with the preservation of biotin binding sites on a streptavidin-targeting moiety conjugate.

The second approach for improving targeting moiety-ligand or targeting moiety-anti-ligand conjugate target-to-blood ratio "chases" the conjugate from the circulation through in vivo complexation of conjugate with a molecule constituting or containing the complementary anti-ligand or ligand. When biotinylated antibodies are used as a ligand-targeting moiety conjugate, for example, avidin forms relatively large aggregated species upon complexation with the circulating biotinylated antibody, which aggregated species are rapidly cleared from the blood by the RES uptake. See, for example, U.S. Pat. No. 4,863,713. One problem with this method, however, is the potential for cross-linking and internalizing tumor-bound biotinylated antibody by avidin.

When avidin-targeting moiety conjugates are employed, poly-biotinylated transferrin has been used to form relatively large aggregated species that are cleared by RES uptake. See, for example, Goodwin, *J. Nucl. Med.* 33(10):1816–18, 1992). Poly-biotinylated transferrin also has the potential for cross-linking and internalizing tumor-bound avidinylated-targeting moiety; however. In addition, both "chase" methodologies involve the prolonged presence of aggregated moieties of intermediate, rather than large, size (which are not cleared as quickly as large size particles by RES uptake), thereby resulting in serum retention of subsequently administered ligand-active agent or anti-ligand active agent. Such serum retention unfavorably impacts the target cell-to-blood targeting ratio.

The present invention provides clearing agents of protein and non-protein composition having physical properties facilitating use for in vivo complexation and blood clearance of anti-ligand/ligand (e.g., avidin/biotin)-targeting moiety (e.g., antibody) conjugates. These clearing agents are useful in improving the target:blood ratio of targeting moiety conjugate. Other applications of these clearing agents include lesional imaging or therapy involving blood clots and the like, employing antibody-active agent delivery modalities. For example, efficacious anti-clotting agent provides rapid target localization and high target:non-target targeting ratio. Active agents administered in pretargeting protocols of the present invention using efficient clearing agents are targeted in the desirable manner and are, therefore, useful in the imaging/therapy of conditions such as pulmonary embolism and deep vein thrombosis.

Clearing agents useful in the practice of the present invention preferably exhibit one or more of the following characteristics:

rapid, efficient complexation with targeting moiety-ligand (or anti-ligand) conjugate in vivo;

rapid clearance from the blood of targeting moiety conjugate capable of binding a subsequently administered complementary anti-ligand or ligand containing molecule;

high capacity for clearing (or inactivating) large amounts of targeting moiety conjugate; and low immunogenicity.

Preferred clearing agents include galactose-based and non-galactose based molecules. Protein-type galactose-based clearing agents include proteins having endogenous exposed galactose residues or which have been derivitized to expose or incorporate such galactose residues. Exposed galactose residues direct the clearing agent to rapid clearance by endocytosis into the liver through specific receptors therefor (Ashwell receptors). These receptors bind the clearing agent, and induce endocytosis into the hepatocyte, leading to fusion with a lysosome and recycle of the receptor back to the cell surface. This clearance mechanism is characterized by high efficiency, high capacity and rapid kinetics.

An exemplary clearing agent of the protein-based/galactose-bearing variety is the asialoorosomucoid derivative of human alpha-1acid glycoprotein (orosomucoid, molecular weight=41,000 Dal; isoelectric point=1.8–2.7). The rapid clearance from the blood of asialoorosomucoid has been documented by Galli, et al., *J. of Nucl. Med. Allied Sci.* 32(2): 110–16, 1988.

Treatment of orosomucoid with neuraminidase removes sialic acid residues, thereby exposing galactose residues. Other such derivitized clearing agents include, for example, galactosylated albumin, galactosylated-IgM, galactosylated-IgG, asialohaptoglobin, asialofetuin, asialoceruloplasmin and the like.

In addition, clearing agents based upon human proteins, especially human serum proteins, are less immunogenic upon administration into the serum of a human recipient. Another advantage of using asialoorosomucoid is that human orosomucoid is commercially available from, for example, Sigma Chemical Co, St. Louis,, Mo.

One way to prevent clearing agent compromise of target-bound conjugate through direct complexation is through use of a clearing agent of a size sufficient to render the clearing agent less capable of diffusion into the extravascular space and binding to target-associated conjugate. This strategy is useful alone or in combination with the aforementioned recognition that exposed galactose residues direct rapid liver uptake. This size-exclusion strategy enhances the effectiveness of non-galactose-based clearing agents of the present invention. The combination (exposed galactose and size) strategy improves the effectiveness of "protein-type" or "polymer-type" galactose-based clearing agents.

Galactose-based clearing agents include galactosylated, biotinylated proteins (to remove circulating streptavidin-targeting moiety conjugates, for example) of intermediate molecular weight (ranging from about 40,000 to about 200,000 Dal), such as asialoorosomucoid, galactosyl-biotinyl-human serum albumin or other galactosylated and biotinylated derivatives of non-immunogenic soluble-natural proteins, as well as biotin- and galactose-derivitized polyglutamate, polylysine, polyarginine, polyaspartate and the like. High molecular weight moieties (ranging from about 200,000 to about 1,000,000 Dal) characterized by poor target access, including galactosyl-biotinyl-IgM or -IgG (approximately 150,000 Dal) molecules, as well as galactose- and biotin-derivitized transferrin conjugates of human serum albumin, IgG and IgM molecules and the like, can also be used as clearing agents of the claimed invention. Chemically modified polymers of intermediate or high molecular weight (ranging from about 40,000 to about 1,000,000 Dal), such as galactose- and biotin-derivitized dextran, hydroxypropylmethacrylamide polymers, polyvinylpyrrolidone-polystyrene copolymers, divinyl ether-maleic acid copolymers, pyran copolymers, or PEG, also have utility as clearing agents in the practice of the present invention. In addition, rapidly clearing biotinylated liposomes (high molecular weight moieties with poor target access) can be derivitized with galactose and biotin to produce clearing agents for use in the practice of the present invention.

A further class of clearing agents useful in the present invention involve small molecules (ranging from about 500 to about 10,000 Dal) derivitized with galactose and biotin that are sufficiently polar to be confined to the vascular space as an in vivo volume of distribution. More specifically, these agents exhibit a highly charged structure and, as a result, are not readily distributed into the extravascular volume, because they do not readily diffuse across the lipid membranes lining the vasculature. Exemplary of such clearing agents are mono- or poly-biotin-derivitized 6,6'-[(3,3'-dimethyl[1,1'-biphenyl]-4,4'-diyl)bis(azo) bis[4-amino-5-hydroxy-1,3-naphthalene disulfonic acid] tetrasodium salt, mono- or poly-biotinyl-galactose-derivitized polysulfated dextran-biotin, mono- or poly-biotinyl-galactose-derivitized dextran-biotin and the like.

The galactose-exposed or -derivitized clearing agents are capable of (1) rapidly and efficiently complexing with the relevant ligand- or anti-ligand-containing conjugates via ligand-anti-ligand affinity; and (2) clearing such complexes from the blood via the galactose receptor, a liver specific degradation system, as opposed to aggregating into complexes that are taken up by the generalized RES system, including the lung and spleen. Additionally, the rapid kinetics of galactose-mediated liver uptake, coupled with the affinity of the ligand-anti-ligand interaction, allow the use of intermediate or even low molecular weight carriers.

Non-galactose residue-bearing moieties of low or intermediate molecular weight (ranging from about 40,000 to about 200,000 Dal) localized in the blood may equilibrate with the extravascular space and, therefore, bind directly to target-associated conjugate, compromising target localization. In addition, aggregation-mediated clearance mechanisms operating through the RES system are accomplished using a large stoichibmetric excess of clearing agent. In contrast, the rapid blood clearance of galactose-based clearing agents used in the present invention prevents equilibration, and the high affinity ligand-anti-ligand binding allows the use of low stoichiometric amounts of such galactose-based clearing agents. This feature further diminishes the potential for galactose-based clearing agents to compromise target-associated conjugate, because the absolute amount of such clearing agent administered is decreased.

Protein-type and polymer-type non-galactose-based clearing agents include the agents described above, absent galactose exposure or derivitization and the like. These clearing agents act through an aggregation-mediated RES mechanism. In these embodiments of the present invention, the clearing agent used will be selected on the basis of the target organ to which access of the clearing agent is to be excluded. For example, high molecular weight (ranging from about 200,000 to about 1,000,000 Dal) clearing agents will be used when tumor targets or clot targets are involved.

Another class of clearing agents includes agents that do not remove circulating ligand or anti-ligand/targeting moiety-conjugates, but instead "inactivate" the circulating conjugates by blocking the relevant anti-ligand or ligand binding sites thereon. These "cap-type" clearing agents are preferably small (500 to 10,000 Dal) highly charged molecules, which exhibit physical characteristics that dictate a volume of distribution equal to that of the plasma compartment (i.e., do not extravasate into the extravascular fluid volume). Exemplary cap-type clearing agents are poly-biotin-derivitized 6,6'-[(3,3'-dimethyl[1,1'-biphenyl]-4,4'-diyl)bis(azo) bis[4-amino-5-hydroxy-1,3-naphthalene disulfonic acid] tetrasodium salt, poly-biotinyl-derivitized polysulfated dextran-biotin, mono- or poly-biotinyl-derivitized dextran-biotin and the like.

Cap-type clearing agents are derivitized with the relevant anti-ligand or ligand, and then administered to a recipient of previously administered ligand/or anti-ligand/targeting moiety conjugate. Clearing agent-conjugate binding therefore diminishes the ability of circulating conjugate to bind any subsequently administered active agent-ligand or active agent-anti-ligand conjugate. The ablation of active agent binding capacity of the circulating conjugate increases the efficiency of active agent delivery to the target, and increases the ratio of target-bound active agent to circulating active agent by preventing the coupling of long-circulating serum protein kinetics with the active agent. Also, confinement of the clearing agent to the plasma compartment prevents compromise of target-associated ligand or anti-ligand.

One embodiment of the present invention in which rapid acting clearing agents are useful is in the delivery of Auger emitters, such as I-125, I-123, Er-165, Sb-119, Hg-197, Ru-97, Tl-201 and I-125 and Br-77, or nucleus-binding drugs to target cell nuclei. In these embodiments of the present invention, targeting moieties that localize to internalizing receptors on target cell surfaces are employed to deliver a targeting moiety-containing conjugate (i.e., a targeting moiety-anti-ligand conjugate in the preferred two-step protocol) to the target cell population. Such internalizing receptors include EGF receptors, transferrin receptors, HER2 receptors, IL-2 receptors, other interleukins and cluster differentiation receptors, somatostatin receptors, other peptide binding receptors and the like.

After the passage of a time period sufficient to achieve localization of the conjugate to target cells, but insufficient to induce internalization of such targeted conjugates by those cells through a receptor-mediated event, a rapidly acting clearing agent is administered. In a preferred two-step protocol, an active agent-containing ligand or anti-ligand conjugate, such as a biotin-Auger emitter or a biotin-nucleus acting drug, is administered as soon as the clearing agent has been given an opportunity to complex with circulating targeting moiety-containing conjugate, with the time lag between clearing agent and active agent administration being less than about 24 hours. In this manner, active agent is readily internalized through target cell receptor-mediated internalization. While circulating Auger emitters are thought to be non-toxic, the rapid, specific targeting afforded by the pretargeting protocols of the present invention increases the potential of shorter half-life Auger emitters, such as I-123, which is available and capable of stable binding.

In order to more effectively deliver a therapeutic or diagnostic dose of radiation to a target site, the radionuclide is preferably retained at the tumor cell surface. Loss of targeted radiation occurs as a consequence of metabolic degradation mediated by metabolically active target cell types, such as tumor or liver cells.

Preferable agents and protocols within the present invention are therefore characterized by prolonged residence of radionuclide at the target cell site to which the radionuclide has localized and improved radiation absorbed dose deposition at that target cell site, with decreased targeted radioactivity loss resulting from metabolism. Radionuclides that are particularly amenable to the practice of this aspect of the present invention are rhenium, iodine and like "non +3 charged" radiometals which exist in chemical forms that easily cross cell membranes and are not, therefore, inherently retained by cells. In contrast, radionuclides having a +3 charge, such as In-111, Y-90, Lu-177 and Ga-67, exhibit natural target cell retention as a result of their containment in high charge density chelates.

Evidence exists that streptavidin is resistant to metabolic degradation. Consequently, radionuclides bound directly or indirectly to streptavidin, rather than, for example, directly to the targeting moiety, are retained at target cell sites for extended periods of time, as described below in Examples XIV and XV. Streptavidin-associated radionuclides can be administered in pretargeting protocols or injected directly into lesions.

In addition, streptavidin-associated radionuclides (e.g., streptavidin-radionuclide and streptavidin-biotin-radionuclide) may be administered as such (in pretargeting protocols) or as conjugates incorporating targeting moieties (intralesional injection and pretargeting protocols) specific for stable target cell surface antigens (such as NR-LU-10 antibody, L6, anti-CEA antibodies or the like) or target cell internalizing antigens (such as anti-HER2$^{neu}$; anti-epidermal growth factor; anti-Lewis Y, including B-1, B-3, BR-64, BR-96 and the like; or the like) to target the streptavidin to the appropriate target cell population.

Streptavidin associated-radionuclides are amenable, for example, to intralesional injection of ovarian cancer lesions studded on the peritoneum and accessible via laparotomy. Another example of an intralesional injection aspect of the present invention involves hepatoma or liver cancer, preferably using a terminal galactose-streptavidin derivative to bind a radionuclide.

Moreover, high molecular weight carriers, such as biodegradable particles, dextran, albumin or the like, may be employed (e.g., conjugated to streptavidin) to limit leakage of the administered streptavidin from the injection site. Alternatively, such carriers are biotinylated, thereby constituting suitable targets or carriers for radionuclide-streptavidin molecules.

The use of streptavidin-associated radionuclides in intralesional injection protocols provides the following advantages:
  less radionuclide is used to better advantage, because the therapeutic efficacy of the administered radionuclide is improved as a result of retention at the target cell site;
  microdiffusion from the injection site results in expansion of the field of radiation deposition;
  minimized toxicity and higher dose rate radiation are achieved;
  combination with modalities exhibiting disparate toxicity profiles may be useful;
  target sites are imageable post-injection to allow dosimetry determinations to be made;
  biodegradable (i.e., not requiring removal) retention moiety-carrier molecules can be utilized; and
  repeated doses can be injected, because local administration without systemic distribution minimizes antiglobulin response.

The use of streptavidin-associated radionuclides in pretargeting protocols provides the following advantages:
  less radionuclide is used to better advantage, because the therapeutic efficacy of the administered radionuclide is improved as a result of retention at the target cell site;
  target sites are imageable post-injection to allow dosimetry determinations to be made;
  minimized toxicity and higher dose rate radiation are achieved; and
  combination with modalities exhibiting disparate toxicity profiles may be useful.

In addition, the target cell retention-enhancing aspect of the present invention is applicable to a hybrid pretargeting/intralesional injection protocol. For example, targeting moiety-biotin conjugate is administered and an intralesional injection of streptavidin follows after a time sufficient to permit localization of the targeting moiety-biotin conjugate to target cell sites of reasonably determinable location. Next, a radionuclide-biotin molecule is administered, wherein this administration is conducted by intralesional, intravenous or other convenient route.

Monovalent antibody fragment-streptavidin conjugate may be used to pretarget streptavidin, preferably in additional embodiments of the two-step aspect of the present invention. Exemplary monovalent antibody fragments useful in these embodiments are Fv, Fab, Fab' and the like. Monovalent antibody fragments, typically exhibiting a molecular weight ranging from about 25 kD (Fv) to about 50 kD (Fab, Fab'), are smaller than whole antibody and, therefore, are generally capable of greater target site penetration. Moreover, monovalent binding can result in less binding carrier restriction at the target surface (occurring during use of bivalent antibodies, which bind strongly and adhere to target cell sites thereby creating a barrier to further egress into sublayers of target tissue), thereby improving the homogeneity of targeting.

In addition, smaller molecules are more rapidly cleared from a recipient, thereby decreasing the immunogenicity of the administered small molecule conjugate. A lower percentage of the administered dose of a monovalent fragment conjugate localizes to target in comparison to a whole antibody conjugate. The decreased immunogenicity may permit a greater initial dose of the monovalent fragment conjugate to be administered, however.

A multivalent, with respect to ligand, moiety is preferably then administered. This moiety also has one or more radionuclides associated therewith. As a result, the multivalent moiety serves as both a clearing agent for circulating anti-ligand-containing conjugate (through cross-linking or aggregation of conjugate) and as a therapeutic agent when associated with target bound conjugate. In contrast to the internalization caused by cross-linking described above, cross-linking at the tumor cell surface stabilizes the monovalent fragment-anti-ligand molecule and, therefore, enhances target retention, under appropriate conditions of antigen density at the target cell. In addition, monovalent antibody fragments generally do not internalize as do bivalent or whole antibodies. The difficulty in internalizing monovalent antibodies permits cross-linking by a monovalent moiety serves to stabilize the bound monovalent antibody through multipoint binding. This two-step protocol of the present invention has greater flexibility with respect to dosing, because the decreased fragment immunogenicity allows more streptavidin-containing conjugate, for example, to be administered, and the simultaneous clearance and therapeutic delivery removes the necessity of a separate controlled clearing step.

Another embodiment of the pretargeting methodologies of the present invention involves the route of administration of the ligand- or anti-ligand-active agents. In these embodiments of the present invention, the active agent-ligand (e.g., radiolabeled biotin) or -anti-ligand is administered intraarterially using an artery supplying tissue that contains the target. In the radiolabeled biotin example, the high extraction efficiency provided by avidin-biotin interaction facilitates delivery of very high radioactivity levels to the target cells, provided the radioactivity specific activity levels are high. The limit to the amount of radioactivity delivered therefore becomes the biotin binding capacity at the target (i.e., the amount of antibody at the target and the avidin equivalent attached thereto).

For these embodiments of the pretargeting methods of the present invention, particle emitting therapeutic radionuclides resulting from transmutation processes (without non-radioactive carrier forms present) are preferred. Exemplary radionuclides include Y-90, Re-188, At-211, Bi-212 and the like. Other reactor-produced radionuclides are useful in the practice of these embodiments of the present invention, if they are able to bind in amounts delivering a therapeutically effective amount of radiation to the target. A therapeutically effective amount of radiation ranges from about 1500 to about 10,000 cGy depending upon several factors known to nuclear medicine practitioners.

Intraarterial administration pretargeting can be applied to targets present in organs or tissues for which supply arteries are accessible. Exemplary applications for intraarterial delivery aspects of the pretargeting methods of the present invention include treatment of liver tumors through hepatic artery administration, brain primary tumors and metastases through carotid artery administration, lung carcinomas through bronchial artery administration and kidney carcinomas through renal artery administration. Intraarterial administration pretargeting can be conducted using chemotherapeutic drug, toxin and anti-tumor active agents as discussed below. High potency drugs, lymphokines, such as IL-2 and tumor necrosis factor, drug/lymphokine-carrier-biotin molecules, biotinylated drugs/lymphokines, and drug/lymphokine/toxin-loaded, biotin-derivitized liposomes are exemplary of active agents and/or dosage forms useful for the delivery thereof in the practice of this embodiment of the present invention.

In embodiments of the present invention employing radionuclide therapeutic agents, the rapid clearance of nontargeted therapeutic agent decreases the exposure of non-target organs, such as bone marrow, to the therapeutic agent. Consequently, higher doses of radiation can be administered absent dose limiting bone marrow toxicity. In addition, pretargeting methods of the present invention optionally include administration of short duration bone marrow protecting agents, such as WR 2721. As a result, even higher doses of radiation can be given, absent dose limiting bone marrow toxicity.

While the pretargeting protocols set forth above have been described primarily in combination with delivery of a radionuclide diagnostic or therapeutic moiety, the protocols are amenable to use for delivery of other moieties, including anti-tumor agents, chemotherapeutic drugs and the like. For example, most naturally occurring and recombinant cytokines have short in vivo halflives. This characteristic limits the clinical effectiveness of these molecules, because near toxic doses are often required. Dose-limiting toxicities in humans have been observed upon high dose IL-2 or tumor necrosis factor administrations, for example.

A protocol, such as administration of streptavidin-targeting moiety conjugate followed by administration of biotinylated cytokine, is also contemplated by the present invention. Such pretargeting of anti-ligand serves to improve the performance of cytokine therapeutics by increasing the amount of cytokine localized to target cells.

Streptavidin-antibody conjugates generally exhibit pharmadokinetics similar to the native antibody and localize well to target cells, depending upon their construction. Biotinylated cytokines retain a short in vivo half-life; however, cytokine may be localized to the target as a result of the affinity of biotin for avidin. In addition, biotin-avidin experience a pH-dependent dissociation which occurs at a slow rate, thereby permitting a relatively constant, sustained release of cytokine at the target site over time. Also, cytokines complexed to target cells through biotin-avidin association are available for extraction and internalization by cells involved in cellular-mediated cytotoxicity.

A pre-formed antibody-streptavidin-biotin-cytokine preparation may also be employed in the practice of these methods of the present invention. In addition, a three-step protocol of the present invention may also be employed to deliver a cytokine, such as IL-2, to a target site.

Other anti-tumor agents that may be delivered in accordance with the pretargeting techniques of the present invention are selecting, including L-selectin, P-selectin and E-selectin. The presence of cytokines stimulates cells, such as endothelial cells, to express selecting on the surfaces thereof. Selectins bind to white blood cells and aid in delivering white blood cells where they are needed. Consequently, a protocol, such as administration of streptavidin- or avidin-targeting moiety conjugate followed by administration of biotinylated selecting, is also contemplated by the present invention. Such pretargeting of anti-ligand serves to improve the performance of selectin therapeutics by increasing the amount of selectin localized to target cells. In this manner, the necessity of cytokine induction of selectin expression is obviated by the localization and retention of selectin at a target cell population.

Chemotherapeutic drugs also generally exhibit short in vivo half-lives at a therapeutically effective dose. Consequently, another example of a protocol of the present invention includes administration of avidin-targeting moiety conjugate followed by administration of a biotin-chemotherapeutic drug conjugate or complex, such as a drug-carrier-biotin complex. A three-step protocol of the present invention may also be employed to deliver a chemotherapeutic drug, such as methotrexate, adriamycin, high potency adriamycin analogs, trichothecenes, potent enediynes, such as esperamycins and calicheamycins, cytoxan, vinca alkaloids, actinamycin D, taxol, taxotere or the like to a target site.

The invention is further described through presentation of the following examples. These examples are offered by way of illustration, and not by way of limitation.

EXAMPLE I

Synthesis of a Chelate-Biotin Conjugate

A chelating compound that contains an $N_3S$ chelating core was attached via an amide linkage to biotin. Radiometal labeling of an exemplary chelate-biotin conjugate is illustrated below.

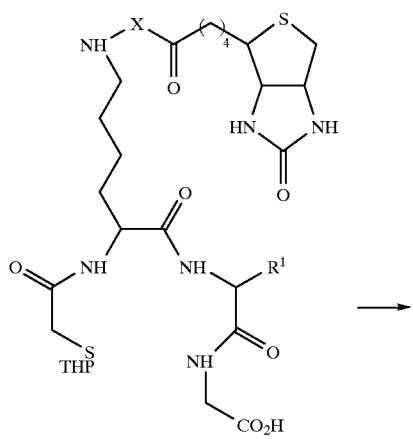

X = $((CH_2)_0$, short chain
X = $CO(CH_2)_5NH$, long chain
$R^1$ = H or $CH_2CO_2H$ -continued

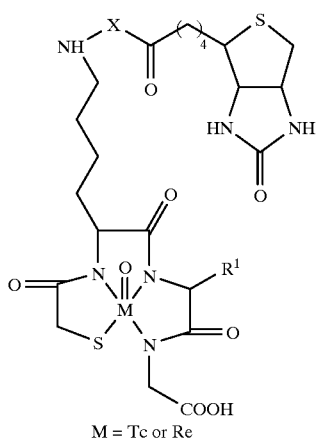

M = Tc or Re

The spacer group "X" permits the biotin portion of the conjugate to be sterically available for avidin binding. When "$R^1$" is a carboxylic acid substituent (for instance, $CH_2COOH$), the conjugate exhibits improved water solubility, and further directs in vivo excretion of the radiolabeled biotin conjugate toward renal rather than hepatobiliary clearance.

Briefly, N-α-Cbz-N-Σ-t-BOC protected lysine was converted to the succinimidyl ester with NHS and DCC, and then condensed with aspartic acid β-t-butyl ester. The resultant dipeptide was activated with NHS and DCC, and then condensed with glycine t-butyl ester. The Cbz group was removed by hydrogenolysis, and the amine was acylated using tetrahydropyranyl mercaptoacetic acid succinimidyl ester, yielding S-(tetrahydropyranyl)-mercaptoacetyl-lysine. Trifluoroacetic acid cleavage of the N-T-BOC group and t-butyl esters, followed by condensation with LC-biotin-NHS ester provided (Σ-caproylamide biotin)-aspartyl glycine. This synthetic method is illustrated below.

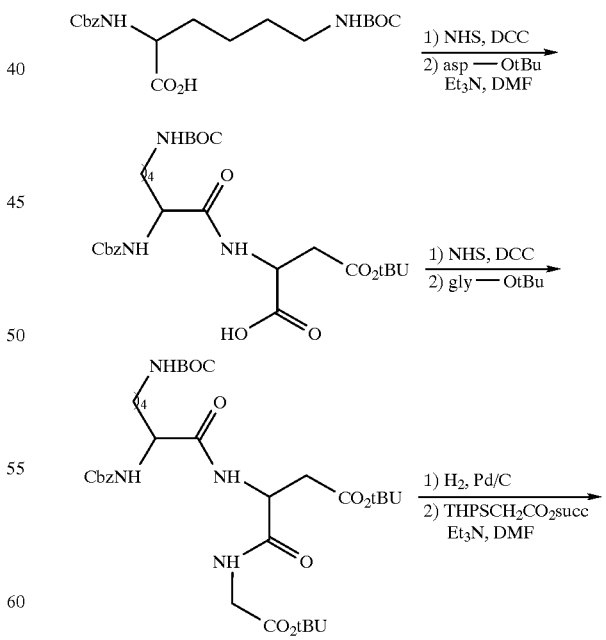

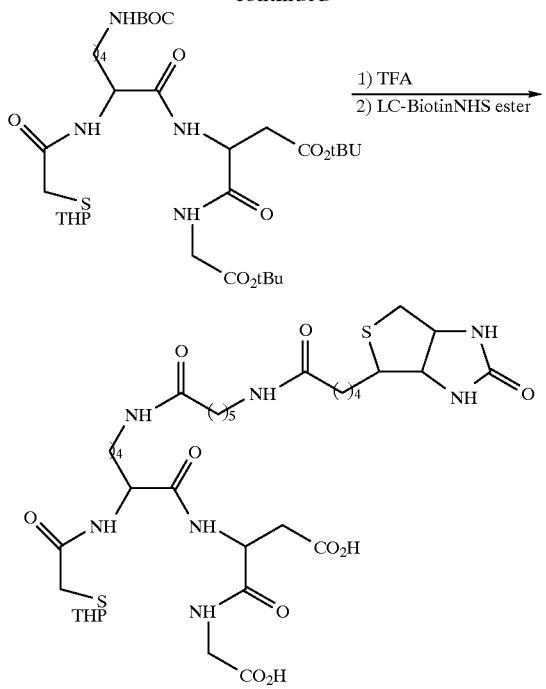

$^1$H NMR: (CD$_3$OD, 200 MHz Varian): 1.25–1.95 (m; 24H), 2.15–2.25 (broad t, 4H), 2.65–3.05 (m, 4H), 3.30–3.45 (dd, 2H), 3.50–3.65 (ddd, 2H), 3.95 (broad s, 2H), 4.00–4.15 (m, 1H), 4.25–4.35 (m; 1H), 4.45–4.55 (m, 1H), 4.7–5.05 (m overlapping with HOD).

Elemental Analysis: C, H, N for C$_{35}$H$_{57}$N$_7$O$_{11}$S$_2$.H$_2$O calculated: 50.41, 7.13, 11.76 found: 50.13, 7.14, 11.40

EXAMPLE II

Preparation of a Technetium or Rhenium Radolabeled Chelate-Biotin Conjugate

The chelate-biotin conjugate of Example I was radiolabeled with either $^{99m}$Tc pertechnetate or $^{186}$Re perrhenate. Briefly, $^{99m}$Tc pertechnetate was reduced with stannous chloride in the presence of sodium gluconate to form an intermediate Tc-gluconate complex. The chelate-biotin conjugate of Example I was added and heated to 100° C. for 10 min at a pH of about 1.8 to about 3.3. The solution was neutralized to a pH of about 6 to about 8, and yielded an N$_3$S-coordinated $^{99m}$Tc-chelate-biotin conjugate. C-18 HPLC gradient elution using 5–60% acetonitrile in 1% acetic acid demonstrated two anomers at 97% or greater radiochemical yield using δ (gamma ray) detection.

Alternatively, $^{186}$Re perrhenate was spiked with cold ammonium perrhenate, reduced with stannous chloride, and complexed with citrate. The chelate-biotin conjugate of Example I was added and heated to 90° C. for 30 min at a pH of about 2 to 3. The solution was neutralized to a pH of about 6 to about 8, and yielded an N$_3$S-coordinated $^{186}$Re-chelate-biotin conjugate. C-18 HPLC gradient elution using 5–60% acetonitrile in 1% acetic acid resulted in radiochemical yields of 85–90%. Subsequent purification over a C-18 reverse phase hydrophobic column yielded material of 99% purity.

EXAMPLE III

In Vitro Analysis of Radiolabeled Chelate-Biotin Conjugates

Both the $^{99m}$Tc- and $^{186}$Re-chelate-biotin conjugates were evaluated in vitro. When combined with excess avidin (about 100-fold molar excess), 100% of both radiolabeled biotin conjugates complexed with avidin.

A $^{99m}$Tc-biotin conjugate was subjected to various chemical challenge conditions. Briefly, $^{99m}$Tc-chelate-biotin conjugates were combined with avidin and passed over a 5 cm size exclusion gel filtration column. The radiolabeled biotin-avidin complexes were subjected to various chemical challenges (see Table 1), and the incubation mixtures were centrifuged through a size exclusion filter. The percent of radioactivity retained (indicating avidin-biotin-associated radiolabel) is presented in Table 1. Thus, upon chemical challenge, the radiometal remained associated with the macromolecular complex.

TABLE 1

Chemical Challenge of $^{99m}$Tc-Chelate-Biotin-Avidin Complexes

| Challenge | | % Radioactivity Retained | |
|---|---|---|---|
| Medium | pH | 1 h, 37° C. | 18 h, RT |
| PBS | 7.2 | 99 | 99 |
| Phosphate | 8.0 | 97 | 97 |
| 10 mM cysteine | 8.0 | 92 | 95 |
| 10 mM DTPA | 8.0 | 99 | 98 |
| 0.2M carbonate | 10.0 | 97 | 94 |

In addition, each radiolabeled biotin conjugate was incubated at about 50 μg/ml with serum; upon completion of the incubation, the samples were subjected to instant thin layer chromatography (ITLC) in 80% methanol. Only 2–4% of the radioactivity remained at the origin (i.e., associated with protein); this percentage was unaffected by the addition of exogenous biotin. When the samples were analyzed using size exclusion H-12 PPLC with 0.2 M phosphate as mobile phase, no association of radioactivity with serum macromolecules was observed.

Each radiolabeled biotin conjugate was further examined using a competitive biotin binding assay. Briefly, solutions containing varying ratios of D-biotin to radiolabeled biotin conjugate were combined with limiting avidin at a constant total biotin:avidin ratio. Avidin binding of each radiolabeled biotin conjugate was determined by ITLC, and was compared to the theoretical maximum stoichiometric binding (as determined by the HABA spectrophotometric assay of Green, Biochem. J. 94:23c–24c, 1965). No significant difference in avidin binding was observed between each studied in an animal model of a three-step antibody radiolabeled biotin conjugate and D-biotin.

EXAMPLE IV

In Vivo Analysis of Radiolabeled Chelate-Biotin Conjugates Administered After Antibody Pretargeting The $^{186}$Re-chelate-biotin conjugate of Example I was studied in an animal model of a three-step antibody pretargeting protocol. Generally, this protocol monoclonal antibody; (ii) administration of avidin for formation of a "sandwich" at the target site and for clearance of residual circulating biotinylated conjugate for target site localization and rapid blood clearance.

A. Preparation and Characterization of Biotinylated Antibody

Biotinylated NR-LU-10 was prepared according to either of the following procedures. The first procedure involved derivitization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO, according to the scheme below.

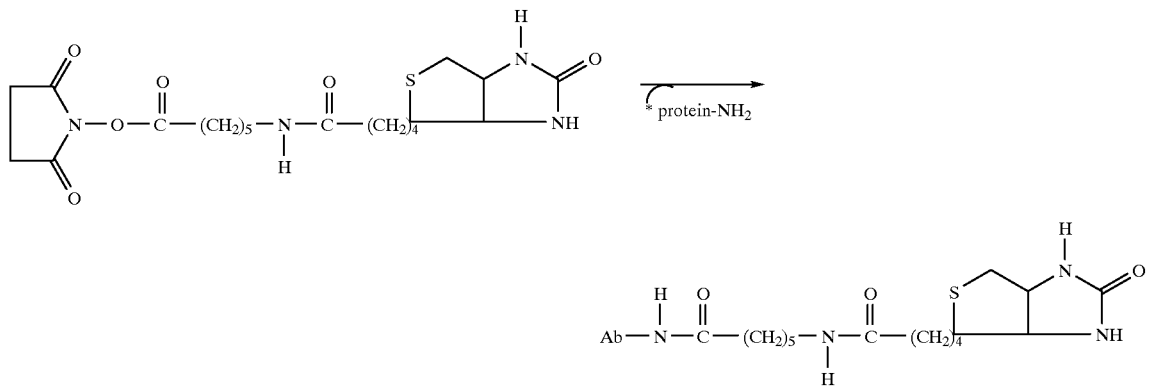

The impact of lysine biotinylation on antibody immunoreactivity was examined. As the molar offering of biotinantibody increased from 5:1 to 40:1, biotin incorporation increased as expected (measured using the HABA assay and pronase-digested product) (Table 2, below). Percent of biotinylated antibody immunoreactivity as compared to native antibody was assessed in a limiting antigen ELISA assay. The immunoreactivity percentage dropped below 70% at a measured derivitization of 11.1:1; however, at this level of derivitization, no decrease was observed in antigen-positive cell binding (performed with LS-180 tumor cells at antigen excess). Subsequent experiments used antibody derivitized at a biotinoantibody ratio of 10:1.

TABLE 2

Effect of Lysine Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivitization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

TABLE 3

Effect of Thiol Biotinylation on Immunoreactivity

| Molar Offering | Measured Derivitization | Immunoassessment (%) | |
|---|---|---|---|
| (Biotins/Ab) | (Biotins/Ab) | ELISA | Cell Binding |
| 10:1 | 4.7 | 114 | |
| 50:1 | 6.5 | 102 | 100 |
| 100:1 | 6.1 | 95 | 100 |

As shown in Table 3, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively) were compared. Molecular sizing on size exclusion FPLC demonstrated that both biotinylation protocols yielded monomolecular (monomeric) IgGs. Biotinylated antibody (lysine) had an apparent molecular weight of 160 kD, while biotinylated antibody (thiol) had an apparent molecular weight of 180 kD. Reduction of endogenous sulfhydryls to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 μg/ml radiolabeled streptavidin was combined with 50 μg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody (lysine)-streptavidin complex.

B. Blood Clearance of Biotinylated Antibody Species

Radioiodinated biotinylated NR-LU-10 (lysine or thiol) was intravenously administered to non-tumored nude mice at a dose of 100 µg. At 24 h post-administration of radioiodinated biotinylated NR-LU-10, mice were intravenously injected with either saline or 400 µg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complex ed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood (see FIG. 1); and increased the level of biotinylated antibody in the liver and spleen. Kidney levels of biotinylated antibody were similar.

EXAMPLE V

In Vivo Characterization of $^{186}$Re-Chelate-Biotin Conjugates In a Three-Step Pretargeting Protocol A $^{186}$Re-chelate-biotin conjugate of Example I (MW≈1000; specific activity=1–2 mCi/mg) was examined in a three-step pretargeting protocol in an animal model. More specifically, 18–22 g female nude mice were implanted subcutaneously with LS-180 human colon tumor xenografts, yielding 100–200 mg tumors within 10 days of implantation.

NR-LU-10 antibody (MW≈150 kD) was radiolabeled with $^{125}$I/Chloramine T and -biotinylated via lysine residues (as described in Example IV.A, above). Avidin (MW≈66 kD) was radiolabeled with $^{131}$I/PIP-NHS (as described for radioiodination of NR-LU-10 in Example IV.A., above). The experimental protocol was as follows:

| | |
|---|---|
| Group 1: | Time 0, inject 100 µg $^{125}$I-labeled, biotinylated NR-LU-10 |
| | Time 24 h, inject 400 µg $^{131}$I-labeled avidin |
| | Time 26 h, inject 60 µg $^{186}$Re-chelate-biotin conjugate |
| Group 2: (control) | Time 0, inject 400 µg $^{131}$I-labeled avidin |
| | Time 2 h, inject 60 µg $^{186}$Re-chelate-biotin conjugate |
| Group 3: (control) | Time 0, inject 60 µg $^{186}$Re-chelate-biotin conjugate |

The three radiolabels employed in this protocol are capable of detection in the presence of each other. It is also noteworthy that the sizes of the three elements involved are logarithmically different—antibody≈150,000; avidin≈66,000, and biotin≈1,000. Biodistribution analyses were performed at 2, 6, 24, 72 and 120 h after administration of the $^{186}$-Re-chelate-biotin conjugate.

Certain preliminary studies were performed in the animal model prior to analyzing the $^{186}$Re-chelate-biotin conjugate in a three-step pretargeting protocol. First, the effect of biotinylated antibody on blood clearance of avidin was examined. These experiments showed that the rate and extent of avidin clearance was similar in the presence or absence of biotinylated antibody. Second, the effect of biotinylated antibody and avidin on blood clearance of the $^{186}$Re-chelate-biotin conjugate was examined; blood clearance was similar in the presence or absence of biotinylated antibody and avidin. Further, antibody immunoreactivity was found to be uncompromised by biotinylation at the level tested.

Third, tumor uptake of biotinylated antibody administered at time 0 or of avidin administered at time 24 h was examined. The results of this experimentation are shown in FIG. 1. At 25 h, about 350 pmol/g biotinylated antibody was present at the tumor; at 32 h the level was about 300 pmol/g; at 48 h, about 200 pmol/g; and at 120 h, about 100 pmol/g. Avidin uptake at the same time points was about 250, 150, 50 and 0 pmol/g, respectively. From the same experiment, tumor to blood ratios were determined for biotinylated antibody and for avidin. From 32 h to 120 h, the ratios of tumor to blood were very similar.

Rapid and efficient removal of biotinylated antibody from the blood by complexation with avidin was observed. Within two hours of avidin administration, a 10-fold reduction in blood pool antibody concentration was noted (FIG. 1), resulting in a sharp increase in tumor to blood ratios. Avidin is cleared rapidly, with greater than 90% of the injected dose cleared from the blood within 1 hour after administration. The Re-186-biotin chelate is also very rapidly cleared, with greater than 99% of the injected dose cleared from the blood by 1 hour after administration.

The three-step pretargeting protocol (described for Group 1, above) was then examined. More specifically, tumor uptake of the $^{186}$Re-chelate-biotin conjugate in the presence or absence of biotinylated antibody and avidin was determined. In the absence of biotinylated antibody and avidin, the $^{186}$Re-chelate-biotin conjugate displayed a slight peak 2 h post-injection, which was substantially cleared from the tumor by about 5 h. In contrast, at 2 h post-injection in the presence of biotinylated antibody and avidin (specific), the $^{186}$Re-chelate-biotin conjugate reached a peak in tumor approximately 7 times greater than that observed in the absence of biotinylated antibody and avidin. Further, the specifically bound $^{186}$Re-chelate-biotin conjugate was retained at the tumor at significant levels for more than 50 h. Tumor to blood ratios determined in the same experiment increased significantly over time (i.e., T:B=≈8 at 30 h; ≈15 at 100 h; ≈35 at 140 h).

Tumor uptake of the $^{186}$Re-chelate-biotin conjugate has further been shown to be dependent on the dose of biotinylated antibody administered. At 0 µg of biotinylated antibody, about 200 pmol/g of $^{186}$Re-chelate-biotin conjugate was present at the tumor at 2 h after administration; at 50 µg antibody, about 500 pmol/g of $^{186}$Re-chelate-biotin conjugate; and at 100 µg antibody, about 1,300 pmol/g of $^{186}$Re-chelate-biotin conjugate.

Figure 2:
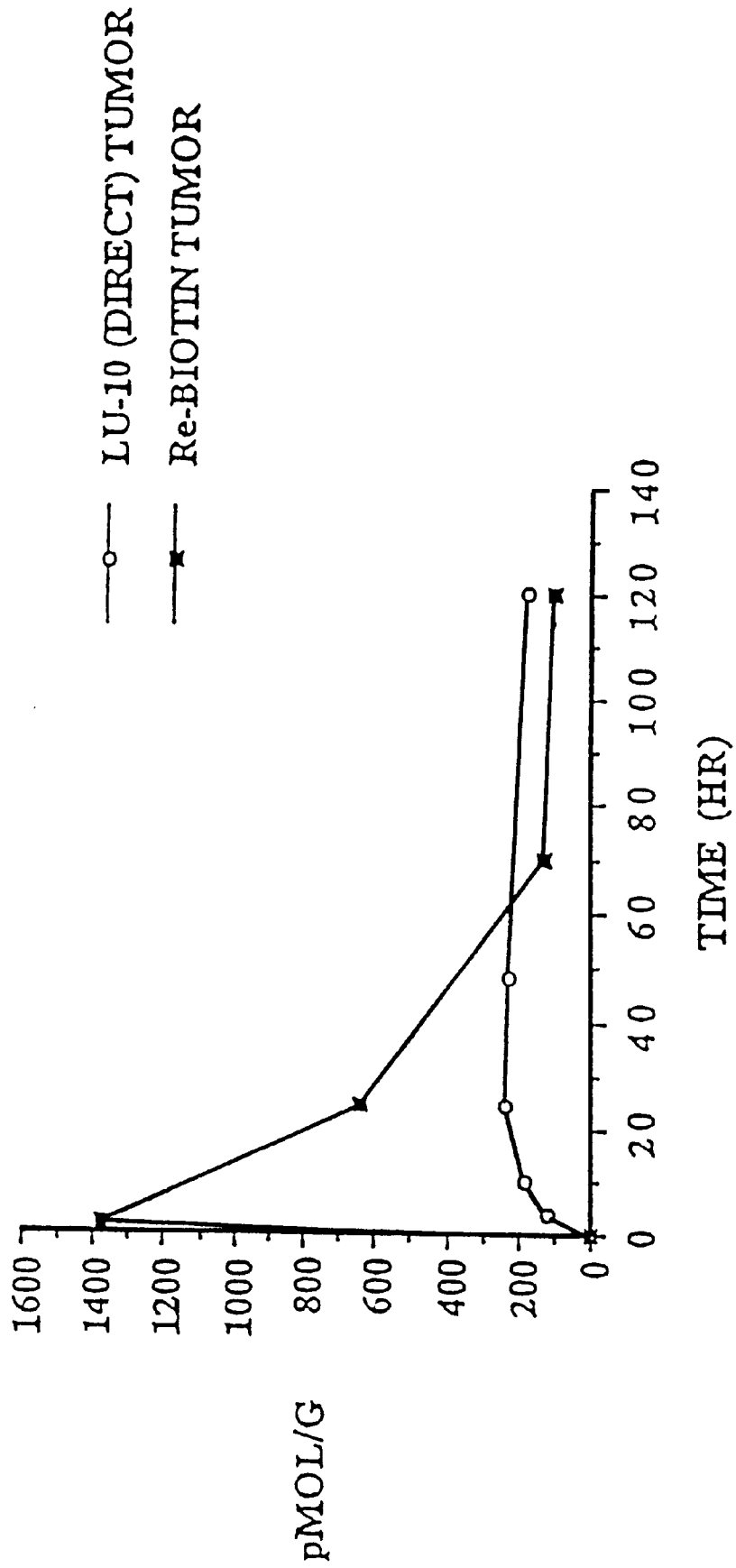
FIG. 2 depicts radiorhenium tumor uptake in a three-step pretargeting protocol, as compared to administration of radiolabeled antibody (conventional means involving antibody that is covalently linked to chelated radiorhenium).

Rhenium tumor uptake via the three-step pretargeting protocol was compared to tumor uptake of the same antibody radiolabeled through chelate covalently attached to the antibody (conventional procedure). The results of this comparison are depicted in FIG. 2. Blood clearance and tumor uptake were compared for the chelate directly labeled rhenium antibody conjugate and for the three-step pretargeted sandwich. Areas under the curves (AUC) and the ratio of $AUC_{tumor}/AUC_{blood}$ were determined. For the chelate directly labeled rhenium antibody conjugate, the ratio of $AUC_{tumor}/AUC_{blood}$=24055/10235 or 2.35; for the three-step pretargeted sandwich, the ratio of $AUC_{tumor}/AUC_{blood}$= 46764/6555 or 7.13.

Tumor uptake results are best taken in context with radioactivity exposure to the blood compartment, which directly correlates with bone marrow exposure. Despite the fact that 100-fold more rhenium was administered to animals in the three-step protocol, the very rapid clearance of the small molecule (Re-186-biotin) from the blood minimizes the exposure to Re-186 given in this manner. In the same matched antibody dose format, direct labeled (conventional procedure) NR-LU-10 whole antibody yielded greater exposure to rhenium than did the 100-fold higher dose given in the three-step protocol. A clear increase in the targeting ratio (tumor exposure to radioactivity:blood exposure to radioactivity—$AUC_{tumor}$:$AUC_{blood}$) was observed for three-step pretargeting (approximately 7:1) in comparison to the direct labeled antibody approach (approximately 2.4:1).

EXAMPLE VI

Preparation of Chelate-Biotin Conjugates Having Improved Biodistribution Properties The biodistribution of $^{111}$In-labeled-biotin derivatives varies greatly with structural changes in the chelate and the conjugating group. Similar structural changes may affect the biodistribution of technetium- and rhenium-biotin conjugates. Accordingly, methods for preparing technetium- and rhenium-biotin conjugates having optimal clearance from normal tissue are advantageous.

A. Neutral MAMA Chelate/Conjugate

A neutral MAMA chelate-biotin conjugate is prepared according to the following scheme.

a) MAMA ligand

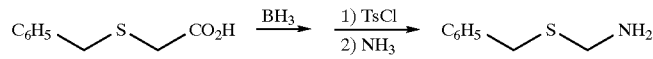

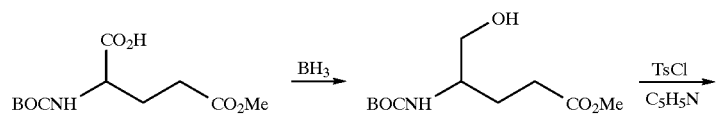

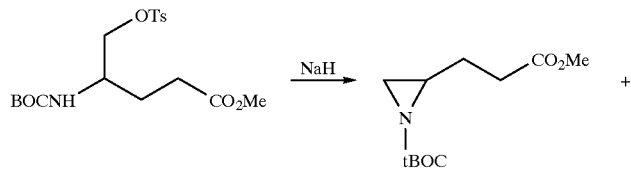

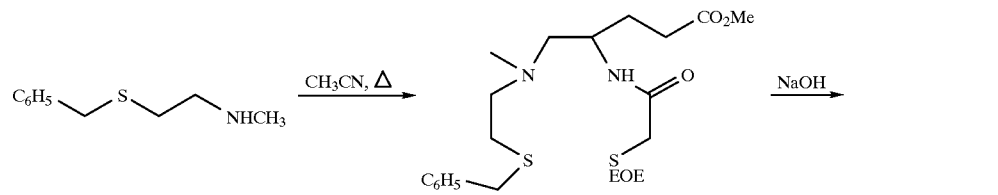

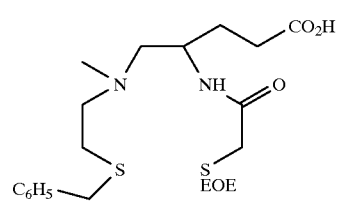

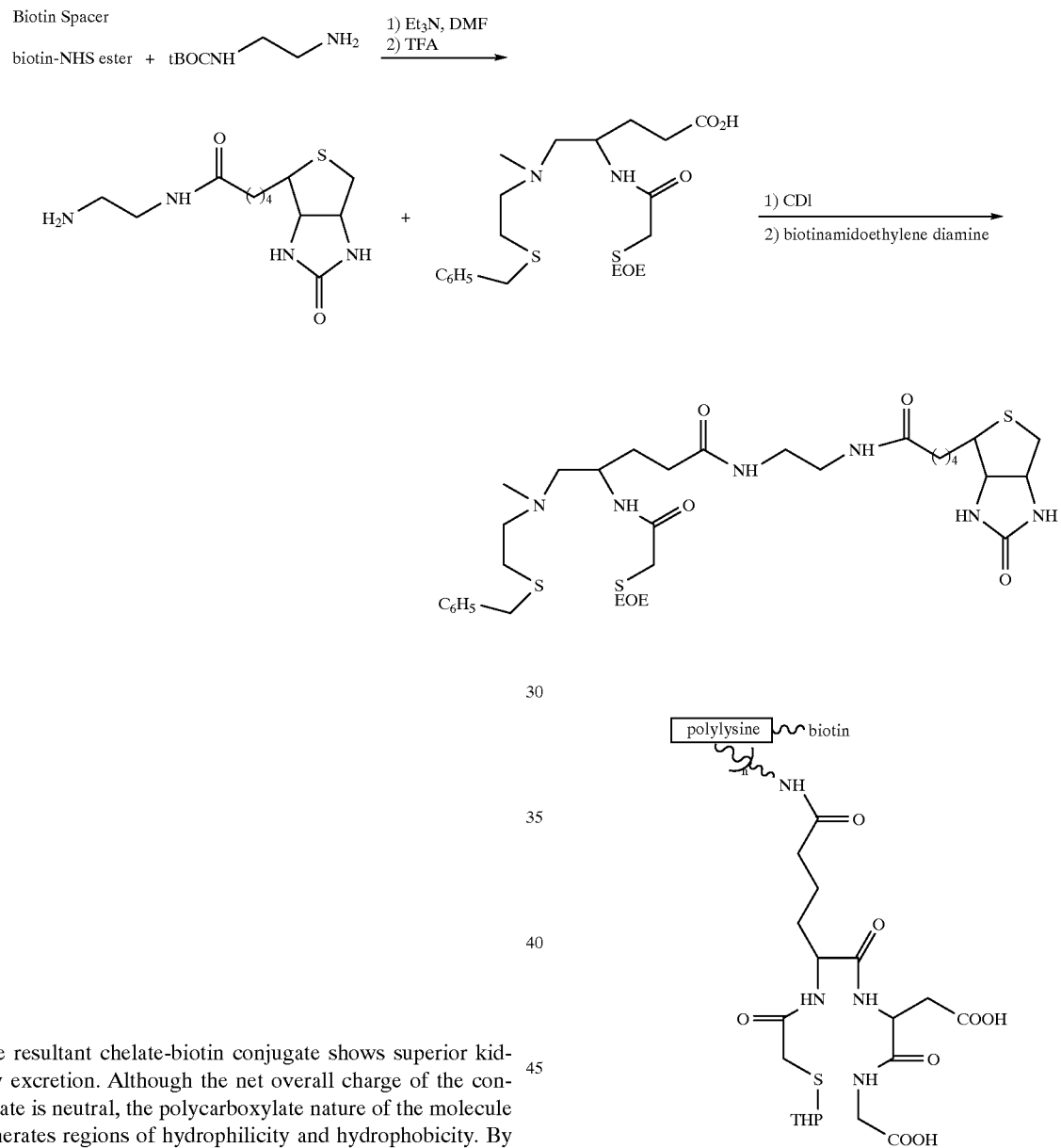

The resultant chelate-biotin conjugate shows superior kidney excretion. Although the net overall charge of the conjugate is neutral, the polycarboxylate nature of the molecule generates regions of hydrophilicity and hydrophobicity. By altering the number and nature of the carboxylate groups within the conjugate, excretion may be shifted from kidney to gastrointestinal routes. For instance, neutral compounds are generally cleared by the kidneys; anionic compounds are generally cleared through the GI system.

B. Polylysine Derivitization

Conjugates containing polylysine may also exhibit beneficial biodistribution properties. With whole antibodies, derivitization with polylysine may skew the biodistribution of conjugate toward liver uptake. In contrast, derivitization of Fab fragments with polylysine results in lower levels of both liver and kidney uptake; blood clearance of these conjugates is similar to that of Fab covalently linked to chelate. An exemplary polylysine derivitized chelate-biotin conjugate is illustrated below.

Inclusion of polylysine in radiometal-chelate-biotin conjugates is therefore useful for minimizing or eliminating RES sequestration while maintaining good liver and kidney clearance of the conjugate. For improved renal excretion properties, polylysine derivatives are preferably succinylated following biotinylation. Polylysine derivatives offer the further advantages of: (1) increasing the specific activity of the radiometal-chelate-biotin conjugate; (2) permitting control of rate and route of blood clearance by varying the molecular weight of the polylysine polymer; and (3) increasing the circulation half-life of the conjugate for optimal tumor interaction.

Polylysine derivitization is accomplished by standard methodologies. Briefly, poly-L-lysine is acylated according to standard amino group acylation procedures (aqueous bicarbonate buffer, pH 8, added biotin-NHS ester, followed by chelate NHS ester). Alternative methodology involves anhydrous conditions using nitrophenyl esters in DMSO and triethyl amine. The resultant conjugates are characterized by UV and NMR spectra.

The number of biotins attached to polylysine is determined by the HABA assay. Spectrophotometric titration is used to assess the extent of amino group derivitization. The radiometal-chelate-biotin conjugate is characterized by size exclusion.

C. Cleavable Linkage

Through insertion of a cleavable linker between the chelate and biotin portion of a radiometal-chelate-biotin conjugate, retention of the conjugate at the tumor relative to normal tissue may be enhanced. More specifically, linkers that are cleaved by enzymes present in normal tissue but deficient or absent in tumor tissue can increase tumor retention. As an example, the kidney has high levels of γ-glutamyl transferase; other normal tissues exhibit in vivo cleavage of γ-glutamyl prodrugs. In contrast, tumors are generally deficient in enzyme peptidases. The glutamyl-linked biotin conjugate depicted below is cleaved in normal tissue and retained in the tumor.

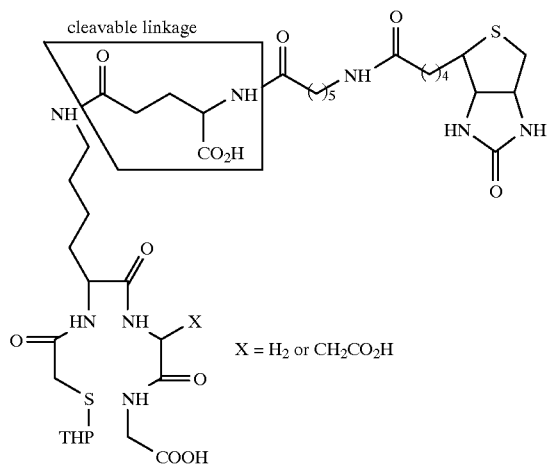

D. Serine Linker With O-Polar Substituent

Sugar substitution of $N_3S$ chelates renders such chelates water soluble. Sulfonates, which are fully ionized at physiological pH, improve water solubility of the chelate-biotin conjugate depicted below.

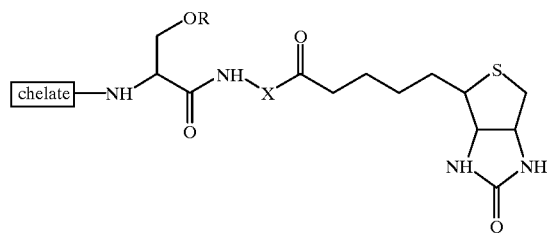

R=a sugar as ribose or glucose or $SO_2OH$ $X=(CH_2)_0$ or $CO(CH:_2)_4$

This compound is synthesized according to the standard reaction procedures. Briefly, biocytin is condensed with N-t-BOC-(O-sulfonate or O-glucose) serine NHS ester to give N-t-BOC-(O-sulfonate or O-glucose) serine biocytinamide. Subsequent cleavage of the N-t-BOC group with TFA and condensation with ligand NHS ester in DMF with triethylamine provides ligand-amidoserine(O-sulfonate or O-glucose)biocytinamide.

EXAMPLE VII

Preparation and Characterization of PIP-Radioiodinated Biotin

Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32:5, 1991, 993 (abstr.)). Because of the high molecular weight of the resultant radioiodinated biotin derivative, only limited characterization of product (i.e., radio-HPLC and binding to immobilized streptavidin) was possible.

Preparation of radioiodinated biotin according to the present invention provides certain advantages. First, the radioiodobiotin derivative is a low molecular weight compound that is amenable to complete chemical characterization. Second, the disclosed methods for preparation involve a single step and eliminate the need for a purification step.

Briefly, iodobenzamide derivatives corresponding to biocytin (R=COOH) and biotinamidopentylamine (R=H) were prepared according to the following scheme. In this scheme, "X" may be any radiohalogen, including $^{125}I$, $^{131}I$, $^{123}I$, $^{211}At$ and the like.

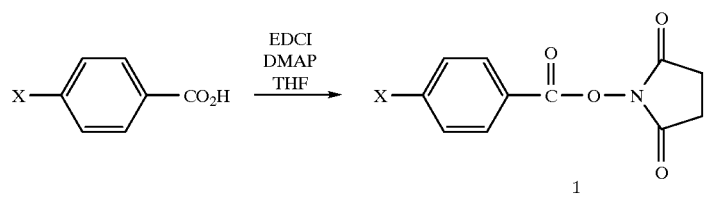

-continued

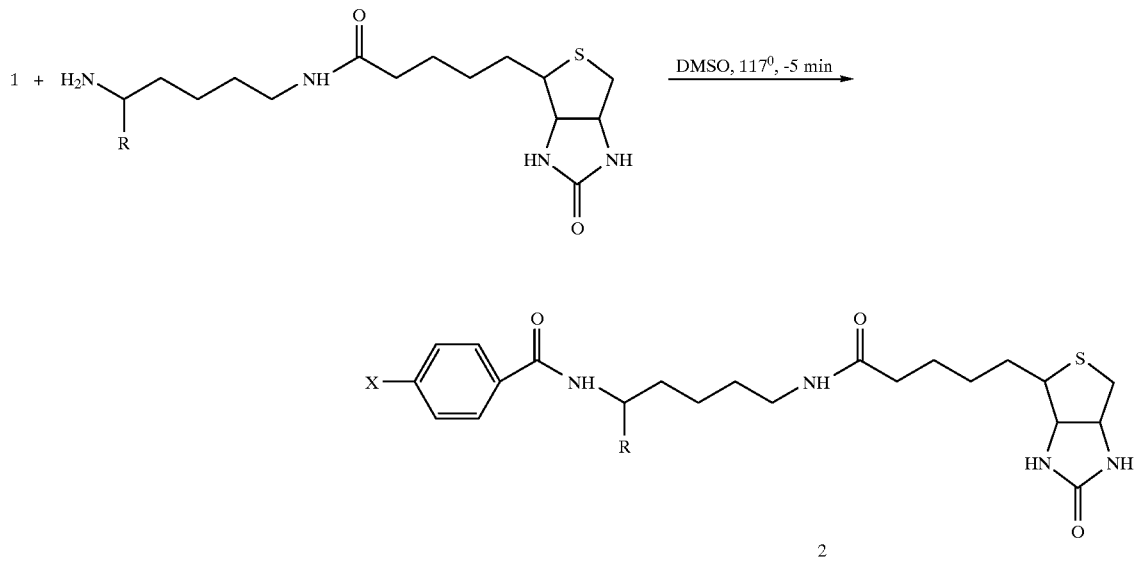

Preparation of 1 was generally according to Wilbur et al., *J. Nucl. Med.* 30:0216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or 5-(biotinamido) pentylamine was sensitive to base. When the reaction of 1 and biocytin or the pentylamine was performed in the presence of triethylamine in hot DMSO, formation of more than one biotinylated product resulted. In contrast, the reaction was extremely clean and complete when a suspension of 1 and biocytin (4 mg/ml) or the pentylamine (4 mg/ml) was heated in DHSO at 117° C. for about 5 to about 10 min. The resultant $^{125}$I-biotin derivatives were obtained in 94% radiochemical yield. Optionally, the radioiodinated products may be purified using C-18 HPLC and a reverse phase hydrophobic column. Hereinafter, the resultant radioiodinated products 2 are referred to as PIP-biocytin (R=COOH) and PIP-pentylamine (R=H).

Both iodobiotin derivatives 2 exhibited ≧95% binding to immobilized avidin. Incubation of the products 2 with mouse serum resulted in no loss of the ability of 2 to bind to immobilized avidin. Biodistribution studies of 2 in male BALB/c mice showed rapid clearance from the blood (similar to $^{186}$Re-chelate-biotin conjugates described above). The radioiodobiotin 2 had decreased hepatobiliary excretion as compared to the $^{186}$Re-chelate-biotin conjugate, urinary excretion was increased as compared to the $^{186}$Re-chelate-biotin conjugate. Analysis of urinary metabolites of 2 indicated deiodination and cleavage of the biotin amide bond; the metabolites showed no binding to immobilized avidin. In contrast, metabolites of the $^{186}$Re-chelate-biotin conjugate appear to be excreted in urine as intact biotin conjugates. Intestinal uptake of 2 is <50% that of the $^{186}$Re-chelate-biotin conjugate. These biodistribution properties of 2 provided enhanced whole body clearance of radioisotope and indicate the advantageous use of 2 within pretargeting protocols.

$^{131}$I-PIP-biocytin was evaluated in a two-step pretargeting procedure in tumor-bearing mice. Briefly, female nude mice were injected subcutaneously with LS-180 tumor cells; after 7 d, the mice displayed 50–100 mg tumor xenografts. At t=0, the mice were injected with 200 μg of NR-LU-10-avidin conjugate labeled with $^{125}$I using PIP-NHS (see Example IV.A.). At t=36 h, the mice received 42 μg of $^{131}$I-PIP-biocytin. The data showed immediate, specific tumor localization, corresponding to ≈1.5 $^{131}$I-PIP-biocytin molecules per avidin molecule.

The described radiohalogenated biotin compounds are amenable to the same types of modifications described in Example VI above for $^{186}$Re-chelate-biotin conjugates. In particular, the following PIP-polylysine-biotin molecule is made by trace labeling polylysine with $^{125}$I-PIP, followed by extensive biotinylation of the polylysine.

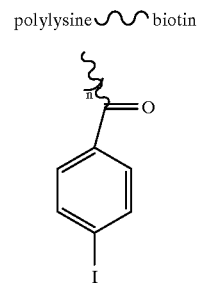

Assessment $^{125}$I binding to immobilized avidin ensures that all radioiodinated species also contain at least an equivalent of biotin.

EXAMPLE VIII

Preparation of Biotinylated Antibody (Thiol) Through Endogenous Antibody Sulfhydryl Groups Or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine (as described in Example IV.A., above). The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

EXAMPLE IX

Two-Step Pretargeting Methodology That Does Not Induce Internalization

A NR-LU-13-avidin conjugate is prepared as follows. Initially, avidin is derivitized with N-succinimidyl 4-(N-maleimidomethyl)cyclohexane-1-carboxylate (SMCC). SMCC-derived avidin is then incubated with NR-LU-13 in a 1:1 molar ratio at pH 8.5 for 16 h. Unreacted NR-LU-13 and SMCC-derived avidin are removed from the mixture using preparative size exclusion HPLC. Two conjugates are obtained as products—the desired 1:1 NR-LU-13-avidin conjugate as the major product; and an incompletely characterized component as the minor product.

A $^{99m}$Tc-chelate-biotin conjugate is prepared as in Example II, above. The NR-LU-13-avidin conjugate is administered to a recipient and allowed to clear from the circulation. One of ordinary skill in the art of radioimmunoscintigraphy is readily able to determine the optimal time for NR-LU-13-avidin conjugate tumor localization and clearance from the circulation. At such time, the $^{99m}$Tc-chelate-biotin conjugate is administered to the recipient. Because the $^{99m}$Tc-chelate-biotin conjugate has a molecular weight of $\approx$1,000, crosslinking of NR-LU-13-avidin molecules on the surface of the tumor cells is dramatically reduced or eliminated. As a result, the $^{99m}$Tc diagnostic agent is retained at the tumor cell surface for an extended period of time. Accordingly, detection of the diagnostic agent by imaging techniques is optimized; further, a lower dose of radioisotope provides an image comparable to that resulting from the typical three-step pretargeting protocol.

Optionally, clearance of NR-LU-13-avidin from the circulation may be accelerated by plasmapheresis in combination with a biotin affinity column. Through use of such column, circulating NR-LU-13-avidin will be retained extracorporeally, and the recipient's immune system exposure to a large, proteinaceous immunogen (i.e., avidin) is minimized.

Clearance of NR-LU-13-avidin may also be accelerated by an arterially inserted proteinaceous or polymeric multiloop device. A catheter-like device, consisting of thin loops of synthetic polymer or protein fibers derivitized with biotin, is inserted into a major artery (e.g., femoral artery) to capture NR-LU-13-avidin. Since the total blood volume passes through a major artery every 70 seconds, the in situ clearing device is effective to reduce circulating NR-LU-13-avidin within a short period of time. This device offers the advantages that NR-LU-13-avidin is not processed through the RES; removal of NR-LU-13-avidin is controllable and measurable; and fresh devices with undiminished binding capacity are insertable as necessary. This methodology is also useful with intraarterial administration embodiments of the present invention.

An alternative procedure for clearing NR-LU-13-avidin from the circulation without induction of internalization involves administration of biotinylated, high molecular weight molecules, such as liposomes, IgM and other molecules that are size excluded from ready permeability to tumor sites. When such biotinylated, high molecular weight molecules aggregate with NR-LU-13-avidin, the aggregated complexes are readily cleared from the circulation via the RES.

EXAMPLE X

Enhancement of Therapeutic Agent Internalization Through Avidin Crosslinking

The ability of multivalent avidin to crosslink two or more biotin molecules (or chelate-biotin conjugates) is advantageously used to improve delivery of therapeutic agents. More specifically, avidin crosslinking induces internalization of crosslinked complexes at the target cell surface.

Biotinylated NR-CO-04 (lysine) is prepared according to the methods described in Example IV.A., above. Doxorubicin-avidin conjugates are prepared by standard conjugation chemistry. The biotinylated NR-CO-04 is administered to a recipient and allowed to clear from the circulation. One of ordinary skill in the art of radioimmunotherapy is readily able to determine the optimal time for biotinylated NR-CO-04 tumor localization and clearance from the circulation. At such time, the doxorubicin-avidin conjugate is administered to the recipient. The avidin portion of the doxorubicin-avidin conjugate crosslinks the biotinylated NR-CO-04 on the cell surface, inducing internalization of the complex. Thus, doxorubicin is more efficiently delivered to the target cell.

In a first alternative protocol, a standard three-step pretargeting methodology is used to enhance intracellular delivery of a drug to a tumor target cell. By analogy to the description above, biotinylated NR-LU-05 is administered, followed by avidin (for blood clearance and to form the middle layer of the sandwich at the target cell-bound biotinylated antibody). Shortly thereafter, and prior to internalization of the biotinylated NR-LU-05-avidin complex; a methotrexate-biotin conjugate is administered.

In a second alternative protocol, biotinylated NR-LU-05 is further covalently linked to methotrexate. Subsequent administration of avidin induces internalization of the complex and enhances intracellular delivery of drug to the tumor target cell.

In a third alternative protocol, NR-CO-04-avidin is administered-to a recipient and allowed to clear from the circulation and localize at the target site. Thereafter, a polybiotinylated species (such as biotinylated poly-L-lysine, as in Example IV.B., above) is administered. In this protocol, the drug to be delivered may be covalently attached to either the antibody-avidin component or to the polybiotinylated species. The polybiotinylated species induces internalization of the (drug)-antibody-avidin-polybiotin-(drug) complex.

EXAMPLE XI

Targeting Moiety-Anti-Ligand Conjugate for Two-Step Pretargeting In Vivo

A. Preparation of SMCC-derivitized streptavidin.

31 mg (0.48 $\mu$mol) streptavidin was dissolved in 9.0 ml PBS to prepare a final solution at 3.5 mg/ml. The pH of the solution was adjusted to 8.5 by addition of 0.9 ml of 0.5 M borate buffer, pH 8.5. A DMSO solution of SMCC (3.5 mg/ml) was prepared, and 477 $\mu$l (4.8 $\mu$mol) of this solution was added dropwise to the vortexing protein solution. After 30 minutes of stirring, the solution was purified by G-25 (PD-10, Pharmacia, Piscataway, N.J.) column chromatography to remove unreacted or hydrolyzed SMCC. The purified SMCC-derivitized streptavidin was isolated (28 mg, 1.67 mg/ml).

B. Preparation of DTT-reduced NR-LU-10. To 77 mg NR-LU-10 (0.42 $\mu$mol) in 15.0 ml PBS was added 1.5 ml of 0.5 M borate buffer, pH 8.5. A DTT solution, at 400 mg/ml (165 μl) was added to the protein solution. After stirring at room temperature for 30 minutes, the reduced antibody was purified by G-25 size exclusion chromatography. Purified DTT-reduced NR-LU-10 was obtained (74 mg, 2.17 mg/ml).

C. Conjugation of SMCC-streptavidin to DTT-reduced NR-LU-10. DTT-reduced NR-LU-10 (63 mg, 29 ml, 0.42 μmol) was diluted with 44.5 ml PBS. The solution of SMCC-streptavidin (28 mg, 17 ml, 0.42 μmol) was added rapidly to the stirring solution of NR-LU-10. Total protein concentration in the reaction mixture was 1.0 mg/ml. The progress of the reaction was monitored by HPLC (Zorbax® GF-250, available from MacMod). After approximately 45 minutes, the reaction was quenched by adding solid sodium tetrathionate to a final concentration of 5 mM.

D. Purification of conjugate. For small scale reactions, monosubstituted conjugate was obtained using HPLC Zorbax (preparative) size exclusion chromatography. The desired monosubstituted conjugate product eluted at 14.0–14.5 min (3.0 ml/min flow rate), while unreacted NR-LU-10 eluted at 14.5–15 min and unreacted derivitized streptavidin eluted at 19–20 min.

For larger scale conjugation reactions, monosubstituted adduct is isolatable using DEAE ion exchange chromatography. After concentration of the crude conjugate mixture, free streptavidin was removed therefrom by eluting the column with 2.5% xylitol in sodium borate buffer, pH 8.6. The bound unreacted antibody and desired conjugate were then sequentially eluted from the column using an increasing salt gradient in 20 mM diethanolamine adjusted to pH 8.6 with sodium hydroxide.

E. Characterization of conjugate.

1. HPLC size exclusion was conducted as described above with respect to small scale purification.

2. SDS-PAGE analysis was performed using 5% polyacrylamide gels under non-denaturing conditions. Conjugates to be evaluated were not boiled in sample buffer containing SDS to avoid dissociation of streptavidin into its 15 kD subunits. Two product bands were observed on the gel, which correspond to the mono- and di-substituted conjugates.

3. Immunoreactivity was assessed, for example, by competitive binding ELISA as compared to free antibody. Values obtained were within 10% of those for the free antibody.

4. Biotin binding capacity was assessed, for example, by titrating a known quantity of conjugate with p-[I-125] iodobenzoylbiocytin. Saturation of the biotin binding sites was observed upon addition of 4 equivalences of the labeled biocytin.

5. In vivo studies are useful to characterize the reaction product, which studies include, for example, serum clearance profiles, ability of the conjugate to target antigen-positive tumors, tumor retention of the conjugate over time and the ability of a biotinylated molecule to bind streptavidin conjugate at the tumor. These data facilitate determination that the synthesis resulted in the formation of a 1:1 streptavidin-NR-LU-10 whole antibody conjugate that exhibits blood clearance properties similar to native NR-LU-10 whole antibody, and tumor uptake and retention properties at least equal to native NR-LU-10.

Figure 3:
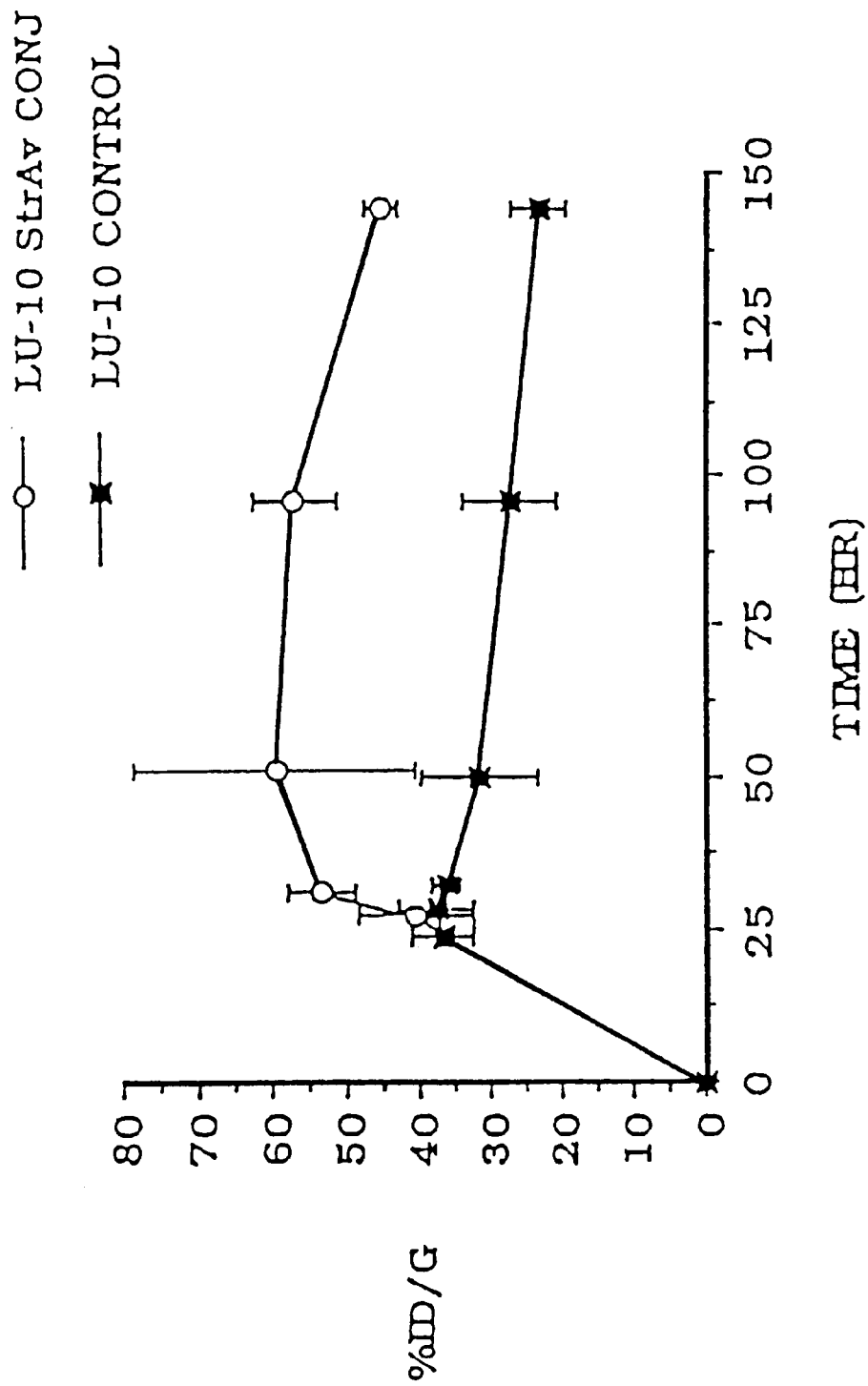
FIG. 3 depicts the tumor uptake profile of NR-LU-10-streptavidin conjugate (LU-10-StrAv) in comparison to a control profile of native NR-LU-10 whole antibody.

For example, FIG. 3 depicts the tumor uptake profile of the NR-LU-10-streptavidin conjugate (LU-10-StrAv) in comparison to a control profile of native NR-LU-10 whole antibody. LU-10-StrAv was radiolabeled on the streptavidin component only, giving a clear indication that LU-10-StrAv localizes to target cells as efficiently as NR-LU-10 whole antibody itself.

EXAMPLE XII

Two-Step Pretargeting In Vivo

A $^{186}$Re-chelate-biotin conjugate (Re-BT) of Example I (MW≈1000; specific activity=1–2 mCi/mg) and a biotin-iodine-131 small molecule, PIP-Biocytin (PIP-BT, MW approximately equal to 602; specific activity=0.5–1.0 mCi/mg), as discussed in Example VII above, were examined in a three-step pretargeting protocol in an animal model, as described in Example V above. Like RE-BT, PIP-BT has the ability to bind well to avidin and is rapidly cleared from the blood, with a serum half-life of about 5 minutes. Equivalent results were observed for both molecules in the two-step pretargeting experiments described herein.

Figure 4:
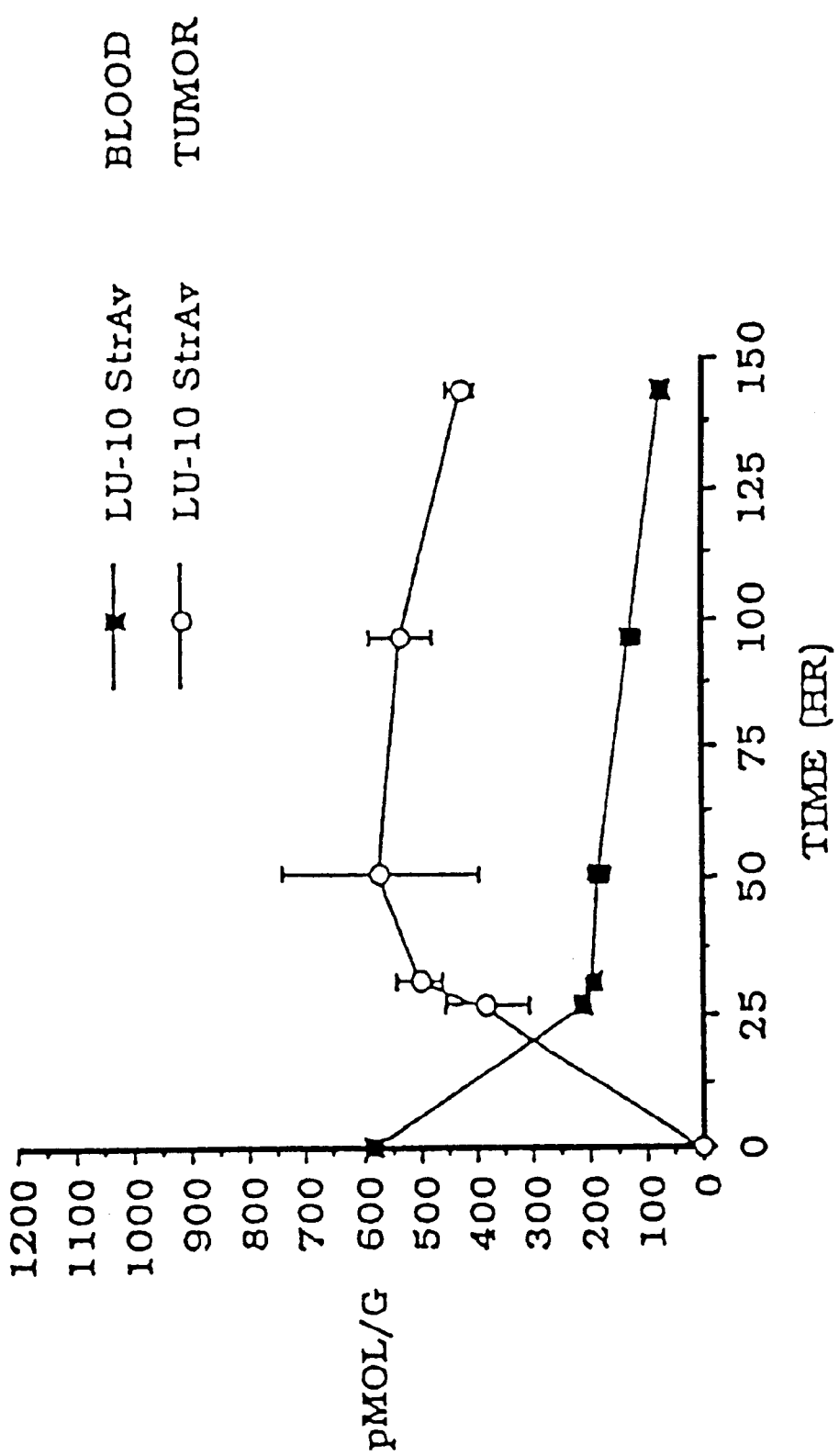
FIG. 4 depicts the tumor uptake and blood clearance profiles of NR-LU-10-streptavidin conjugate.

NR-LU-10 antibody (MW≈150 kD) was conjugated to streptavidin (MW≈66 kD) (as described in Example XI above) and radiolabeled with $^{125}$I/PIP-NHS (as described for radioiodination of NR-LU-10 in Example IV.A., above). The experimental protocol was as follows:

| Time 0 | inject (i.v.) 200 μg NR-LU-10-StrAv conjugate; |
|---|---|
| Time 24–48 h | inject (i.v.) 60–70 fold molar excess of radiolabeled biotinyl molecule; | and perform biodistributions at 2, 6, 24, 72, 120 hours after injection of radiolabeled biotinyl molecule NR-LU-10-streptavidin has shown very consistent patterns of blood clearance and tumor uptake in the LS-180 animal model. A representative profile is shown in FIG. 4. When either PIP-BT or RE-BT is administered after allowing the LU-10-StrAv conjugate to localize to target cell sites for at least 24 hours, the tumor uptake of therapeutic radionuclide is high in both absolute amount and rapidity. For PIP-BT administered at 37 hours following LU-10-StrAv (I-125) administration, tumor uptake was above 500 pMOL/G at the 40 hour time point and peaked at about 700 pMOL/G at 45 hours post-LU-10-StrAv administration.

This almost instantaneous uptake of a small molecule therapeutic into tumor in stoichiometric amounts comparable to the antibody targeting moiety facilitates utilization of the therapeutic radionuclide at its highest specific activity. Also, the rapid clearance of radionuclide that is not bound to LU-10-StrAv conjugate permits an increased targeting ratio (tumor:blood) by eliminating the slow tumor accretion phase observed with directly labeled antibody conjugates. The pattern of radionuclide tumor retention is that of whole antibody, which is very persistent.

Experimentation using the two-step pretargeting approach and progressively lower molar doses of radiolabeled biotinyl molecule was also conducted. Uptake values of about 20% ID/G were achieved at no-carrier added (high specific activity) doses of radiolabeled biotinyl molecules. At less than saturating doses, circulating LU-10-StrAv was observed to bind significant amounts of administered radiolabeled biotinyl molecule in the blood compartment.

EXAMPLE XIII

Asialoorosomucoid Clearing Agent and Two-Step Pretargeting

In order to maximize the targeting ratio (tumor:blood), clearing agents were sought that are capable of clearing the blood pool of targeting moiety-anti-ligand conjugate (e.g., LU-10-StrAv), without compromising the ligand binding capacity thereof at the target sites. One such agent, biotinylated asialoorosomucoid, which employs the avidin-biotin interaction to conjugate to circulating LU-10-StrAv, was tested.

A. Derivitization of orosomucoid. 10 mg human orosomucoid (Sigma N-9885) was dissolved in 3.5 ml of pH 5.5 0.1 M sodium acetate buffer containing 160 mH NaCl. 70 μl of a 2% (w/v) CaCl solution in deionized (D.I.) water was added and 11 μl of neuraminidase (Sigma N-7885), 4.6 U/ml, was added. The mixture was incubated at 37° C. for 2 hours, and the entire sample was exchanged over a Centricon-10® ultrafiltration device (available from Amicon, Danvers, Mass.) with 2 volumes of PBS. The asialoorosomucoid and orosomucoid starting material were radiolabeled with I-125 using PIP technology, as described in Example IV above.

Figure 5:
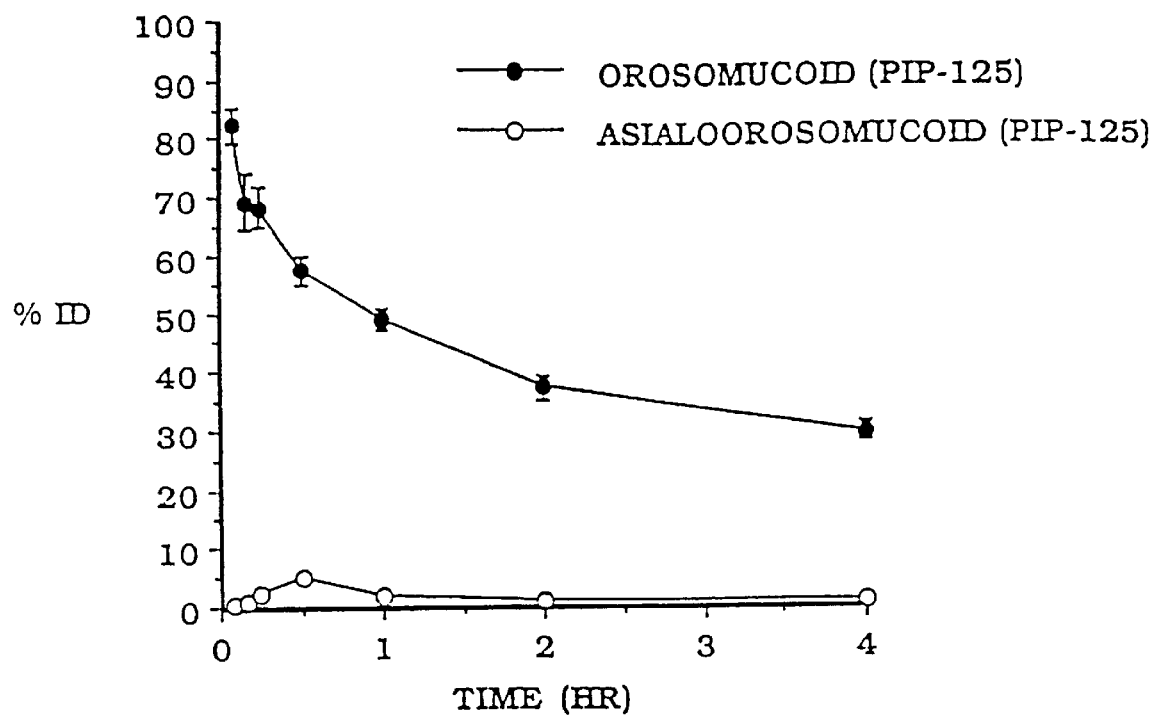
FIG. 5 depicts the rapid clearance from the blood of asialoorosomucoid in comparison with orosomucoid in terms of percent injected dose of I-125-labeled protein.

The two radiolabeled preparations were injected i.v. into female BALB/c mice (20–25 g), and blood clearance was assessed by serial retro-orbital eye bleeding of each group of three mice at 5, 10, 15 and 30 minutes, as well as at 1, 2 and 4 hours post-administration. The results of this experiment are shown in FIG. 5, with asialoorosomucoid clearing more rapidly than its orosomucoid counterpart.

Figure 6:
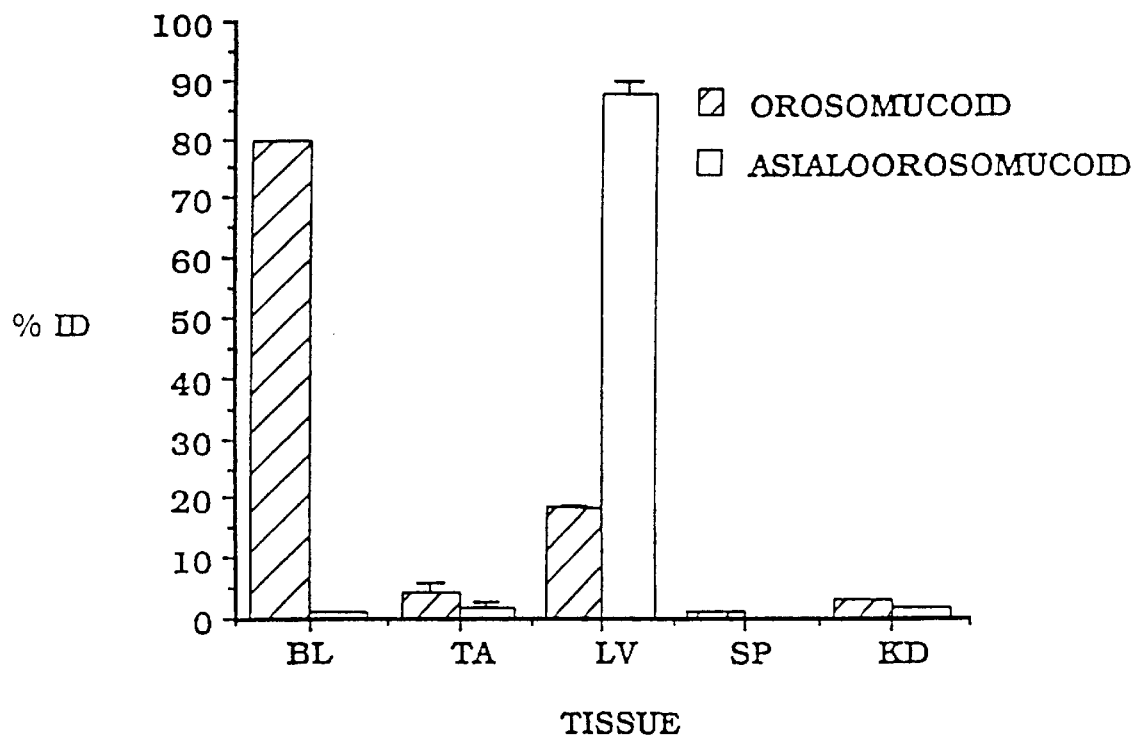
FIG. 6 depicts the 5 minute limited biodistribution of asialoorosomucoid in comparison with orosomucoid in terms of percent injected dose of I-125-labeled protein.

In addition, two animals receiving each compound were sacrificed at 5 minutes post-administration and limited biodistributions were performed. These results are shown in FIG. 6. The most striking aspects of these data are the differences in blood levels (78% for orosomucoid and 0.4% for asialoorosomucoid) and the specificity of uptake of asialoorosomucoid in the liver (86%), as opposed to other tissues.

B. Biotinylation of asialoorosomucoid clearing agent and orosomucoid control. 100 μl of 0.2 M sodium carbonate buffer, pH 9.2, was added to 2 mg (in 1.00 ml PBS) of PIP-125-labeled orosomucoid and to 2 mg PIP-125-labeled asialoorosomucoid. 60 μl of a 1.85 mg/ml solution of NHS-amino caproate biotin in DMSO was then added to each compound. The reaction mixtures were vortexed and allowed to sit at room temperature for 45 minutes. The material was purified by size exclusion column chromatography (PD-10, Pharmacia) and eluted with PBS. 1.2 ml fractions were taken, with fractions 4 and 5 containing the majority of the applied radioactivity (>95%). Streptavidin-agarose beads (Sigma S-1638) or -pellets were washed with PBS; and 20 μg of each biotinylated, radiolabeled protein was added to 400 μl of beads and 400 μl of PBS; vortexed for 20 seconds and centrifuged at 14,000 rpm for 5 minutes. The supernatant was removed and the pellets were washed with 400 μl PBS. This wash procedure was repeated twice more, and the combined supernatants were assayed by placing them in a dosimeter versus their respective pellets. The values are shown below in Table 4.

TABLE 4

| Compound | Supernatant | Pellet |
|---|---|---|
| orosomucoid | 90% | 10% |
| biotin-oroso | 7.7% | 92.% |
| asialoorosomucoid | 92% | 8.0% |
| biotin-asialo | 10% | 90% |

C. Protein-Streptavidin Binding in vivo. Biotin-asialoorosomucoid was evaluated for the ability to couple with circulating LU-10-StrAv conjugate in vivo and to remove it from the blood. Female BALB/c mice (20–25 g) were injected i.v. with 200 μg LU-10-StrAv conjugate. Clearing agent (200 μl PBS—group 1; 400 μg non-biotinylated asialoorosomucoid—group 2; 400 μg biotinylated asialoorosomucoid—group 3, and 200 μg biotinylated asialoorosomucoid—group 4) was administered at 25 hours following conjugate administration. A fifth group received PIP-I-131-LU-10-StrAv conjugate which had been saturated prior to injection with biotin—group 5. The 400 μg dose constituted a 10:1 molar excess of clearing agent over the initial dose of LU-10-StrAv conjugate, while the 200 μg dose constituted a 5:1 molar excess. The saturated PIP-I-131-LU-10-StrAv conjugate was produced by addition of a 10-fold molar excess of D-biotin to 2 mg of LU-10-StrAv followed by size exclusion purification on a G-25 PD-10 column.

Three mice from each group were serially bled, as described above, at 0.17, 1, 4 and 25 hours (pre-injection of clearing agent), as well as at 27, 28, 47, 70 and 90 hours. Two additional animals from each group were sacrificed at 2 hours post-clearing agent administration and limited biodistributions were performed.

Figure 7:
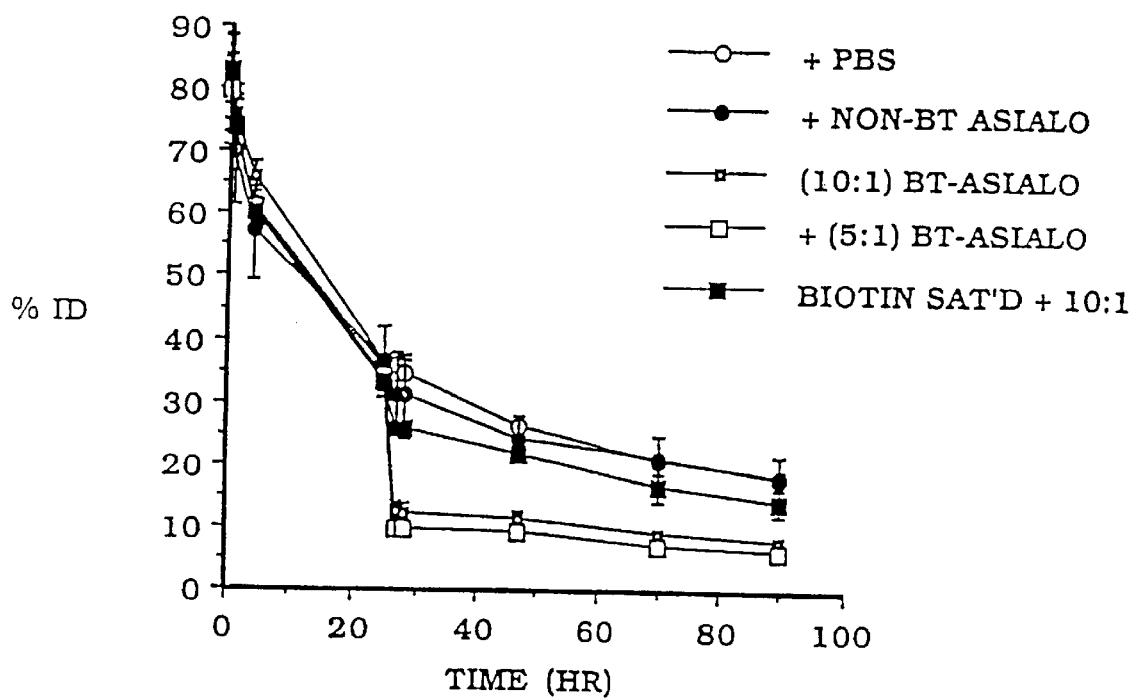
FIG. 7 depicts NR-LU-10-streptavidin conjugate blood clearance upon administration of three controls (○, ●, ■) and two doses of a clearing agent (¤, □) at 25 hours post-conjugate administration.

The blood clearance data are shown in FIG. 7. These data indicate that circulating LU-10-StrAv radioactivity in groups 3 and 4 was rapidly and significantly reduced, in comparison to those values obtained in the control groups 1, 2 and 5. Absolute reduction in circulating antibody-streptavidin conjugate was approximately 75% when compared to controls.

Biodistribution data are shown in tabular form in FIG. 8. The biodistribution data show reduced levels of conjugate for groups 3 and 4 in all tissues except the liver, kidney and intestine, which is consistent with the processing and excretion of radiolabel associated with the conjugate after complexation with biotinylated asialoorosomucoid.

Figure 9:
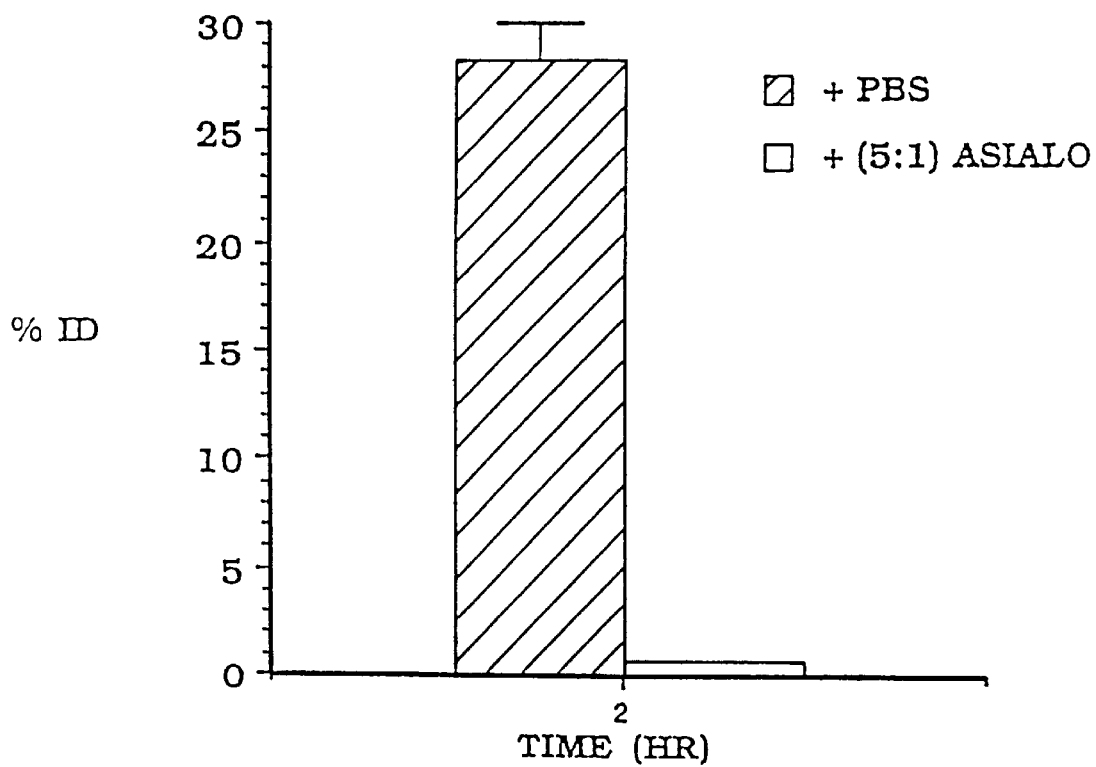
FIG. 9 depicts NR-LU-10-streptavidin conjugate serum biotin binding capability at 2 hours post-clearing agent administration.

Furthermore; residual circulating conjugate was obtained from serum samples by cardiac puncture (with the assays conducted in serum+PBS) and analyzed for the ability to bind biotin (immobilized biotin on agarose beads), an indicator of functional streptavidin remaining in the serum. Group 1 animal serum showed conjugate radiolabel bound about 80% to immobilized biotin. Correcting the residual circulating radiolabel values by multiplying the remaining percent injected dose (at 2 hours after clearing agent administration) by the remaining percent able to bind immobilize biotin (the amount of remaining functional conjugate) leads to the graph shown in FIG. 9. Administration of 200 mg biotinylated asialoorosomucoid resulted in a 50-fold reduction in serum biotin-binding capacity and, in preliminary studies in tumored animals, has not exhibited cross-linking and removal of prelocalized LU-10-StrAv conjugate from the tumor. Removal of circulating targeting moiety-anti-ligand without diminishing biotin-binding capacity at target cell sites, coupled with an increased radiation dose to the tumor resulting from an increase in the amount of targeting moiety-anti-ligand administered, results in both increased absolute rad dose to tumor and diminished toxicity to non-tumor cells, compared to what is currently achievable using conventional radioimmunotherapy.

Figure 10:
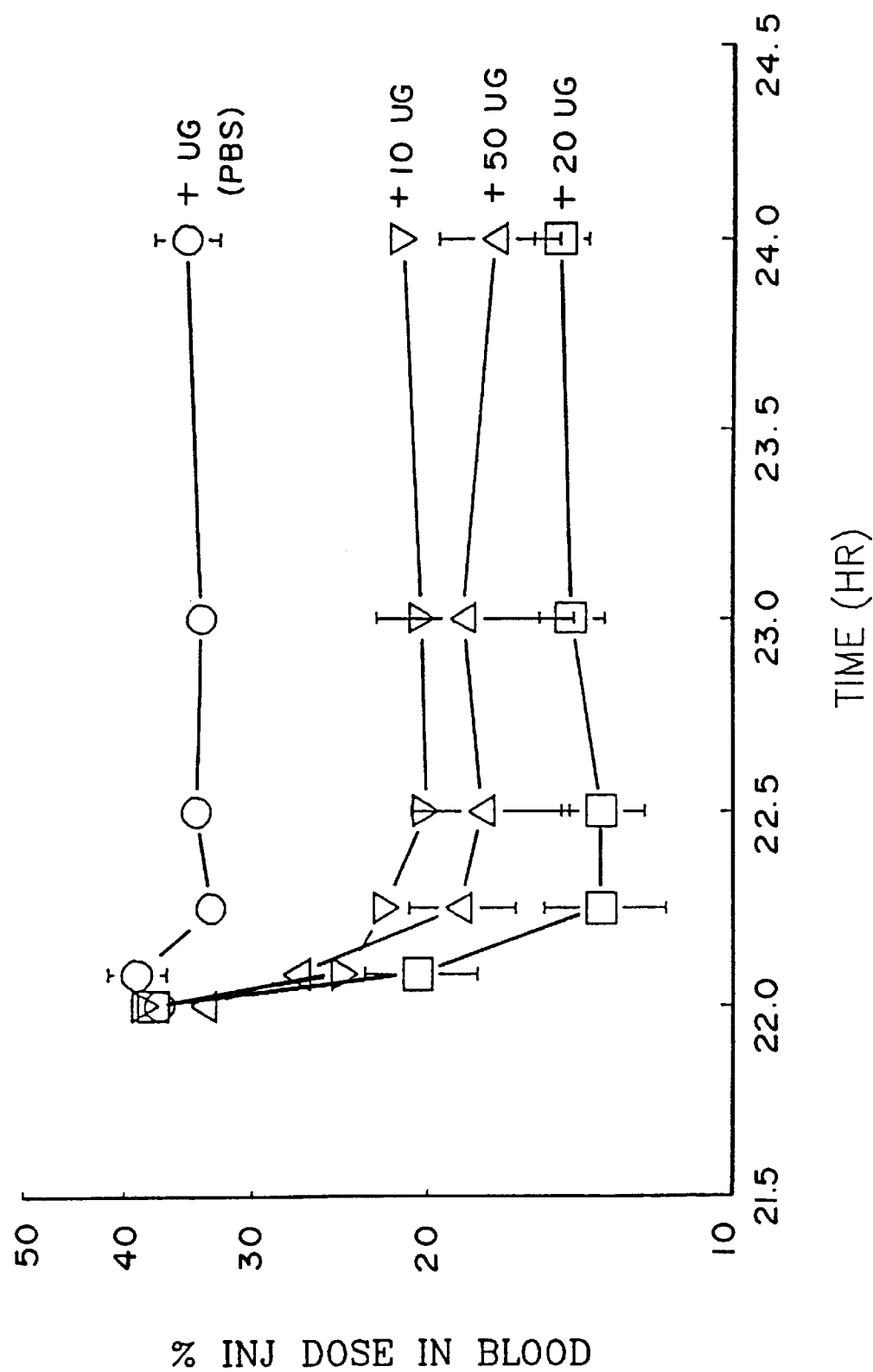
FIG. 10 depicts NR-LU-10-streptavidin conjugate blood clearance over time upon administration of a control (○) and three doses of a clearing agent (∇, Δ, □) at 24 hours post-conjugate administration.
Figure 11B:
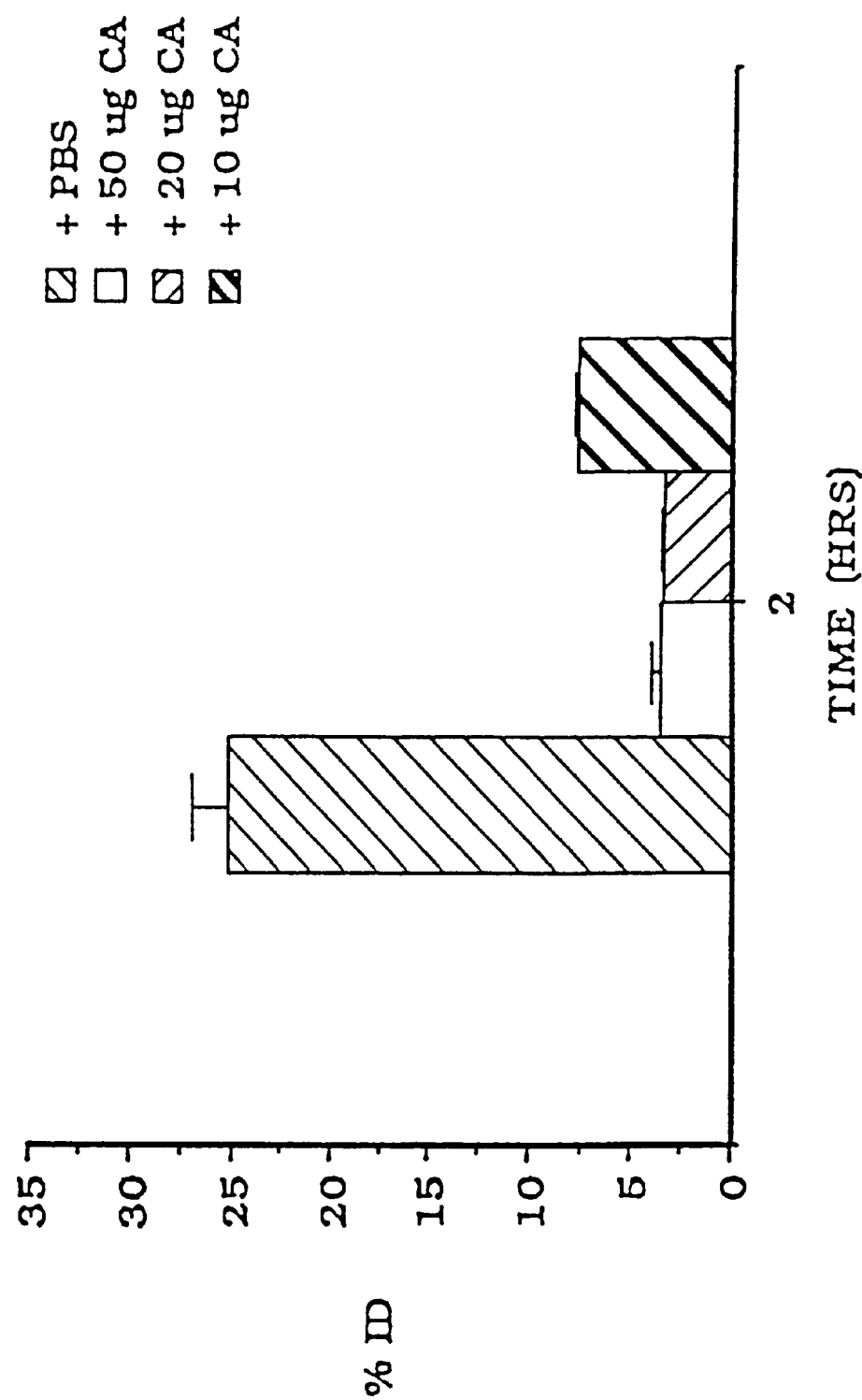
FIG. 11B depicts LU-10-StrAv conjugate serum biotin binding capability upon administration of a control (PBS) and three doses (50, 20 and 10 μg) of clearing agent at two hours post-clearing agent administration.

A subsequent experiment was executed to evaluate lower doses of asialoorosomucoid-biotin. In the same animal model, doses of 50, 20 and 10 μg asialoorosomucoid-biotin were injected at 24 hours following administration of the LU-10-StrAv conjugate. Data from animals serially bled are shown in FIG. 10, and data from animals sacrificed two hours after clearing agent administration are shown in FIGS. 11A (blood clearance) and 11B (serum biotin-binding), respectively. Doses of 50 and 20 μg asialoorosomucoid-biotin effectively reduced circulating LU-10-StrAv conjugate levels by about 65% (FIG. 11A) and, after correction for binding to immobilized biotin, left only 3% of the injected dose in circulation that possessed biotin-binding capacity, compared with about 25% of the injected dose in control animals (FIG. 11B). Even at low doses (approaching 1:1 stoichiometry with circulating LU-10-StrAv conjugate), asialoorosomucoid-biotin was highly effective at reducing blood levels of circulating streptavidin-containing conjugate by an in vivo complexation that was dependent upon biotin-avidin interaction.

EXAMPLE XIV

Streptavidin Anti-Ligand in Tumors

A set of female nude mice, implanted subcutaneously with LS-180 human colon carcinoma xenografts as described above, were randomized into groups of 4 animals/timepoint. The mice were intravenously injected with 200 μg of 1:1 mol/mol NR-LU-10 monoclonal antibody covalently coupled to streptavidin (MAB-STRPT), with the conjugate formed as described in Example XI above. The streptavidin portion of the conjugate was radiolabeled with paraiodophenyl (PIP) I-125, as described in Example IV above. Groups of mice were sacrificed at 26, 30, 48, 96 and 144 hours post-conjugate injection. Tissues were isolated, weighed and counted with respect to iodine radionuclide content using conventional procedures therefor.

A second set of female nude mice bearing LS-180 xenografts were also randomized into groups of 4 animals/timepoint. These mice were intravenously injected with 50 μg of NR-LU-10 monoclonal antibody radiolabeled with paraiodophenyl (PIP) I-131 (MAB), as described in Example IV above. Mice were sacrificed at 4, 24, 48, 128 and 168 hours post-radiolabeled monoclonal antibody injection. Tissues were isolated, weighed and counted with respect to iodine radionuclide content using conventional procedures therefor.

Figure 12:
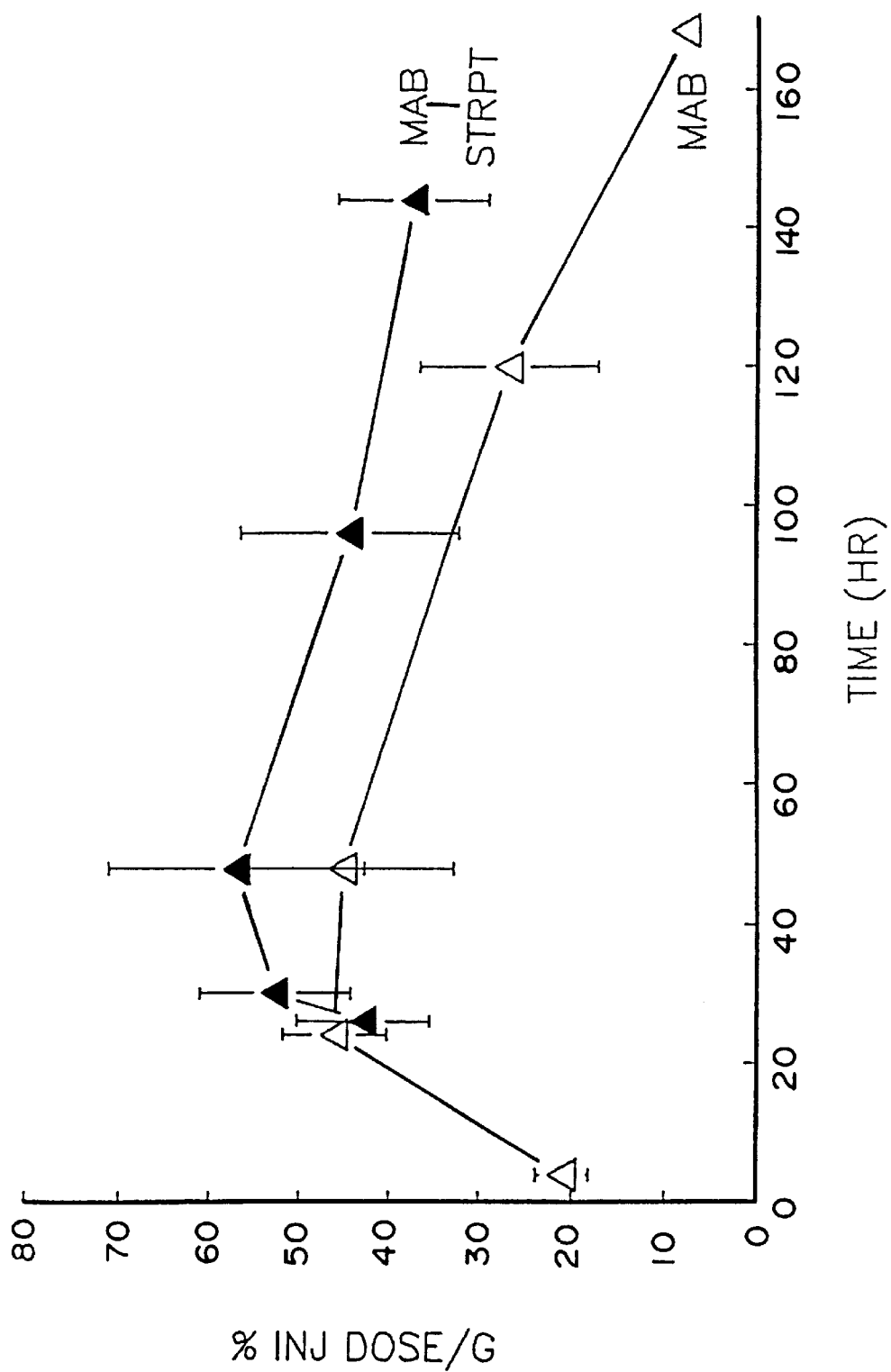
FIG. 12 depicts the prolonged tumor retention of NR-LU-10-streptavidin conjugate (▲) relative to NR-LU-10 whole antibody (Δ) over time.

For each data set, a radioactivity standard of the injected dose was also counted, and data were reduced to a percent of the total injected dose per gram of tissue. FIG. 12 shows the percent injected dose/gram of NR-LU-10-streptavidin-PIP-I-125 and N-RLU-10-PIP-I-131 in LS-180 tumors over time. The NR-LU-10-streptavidin conjugate exhibits higher tumor uptake and a longer retention time as compared to NR-LU-10 alone.

EXAMPLE XV

Streptavidin Ant-Ligand in Liver

Female nude mice xenografted with LS-180 tumor cells, as discussed above, were randomized into groups of 4 animals/timepoint. Mice were intravenously injected with 50 μg of biotinylated NR-LU-10 monoclonal antibody that was non-covalently coupled (to form a complex) through biotin-streptavidin binding to 30 μg of streptavidin. Prior to complexation in vivo, the antibody portion of the complex was radiolabeled with I-125 using chloramine-T, and the streptavidin portion was labeled with paraiodophenyl (PIP) I-131, both of the labeling procedures having been described above. Mice were sacrificed at 4, 24, 48, 96 and 144 hours post-conjugate injection. Tissues were isolated, weighed and counted with respect to the content of each iodine radionuclide using conventional procedures therefor.

Figure 13:
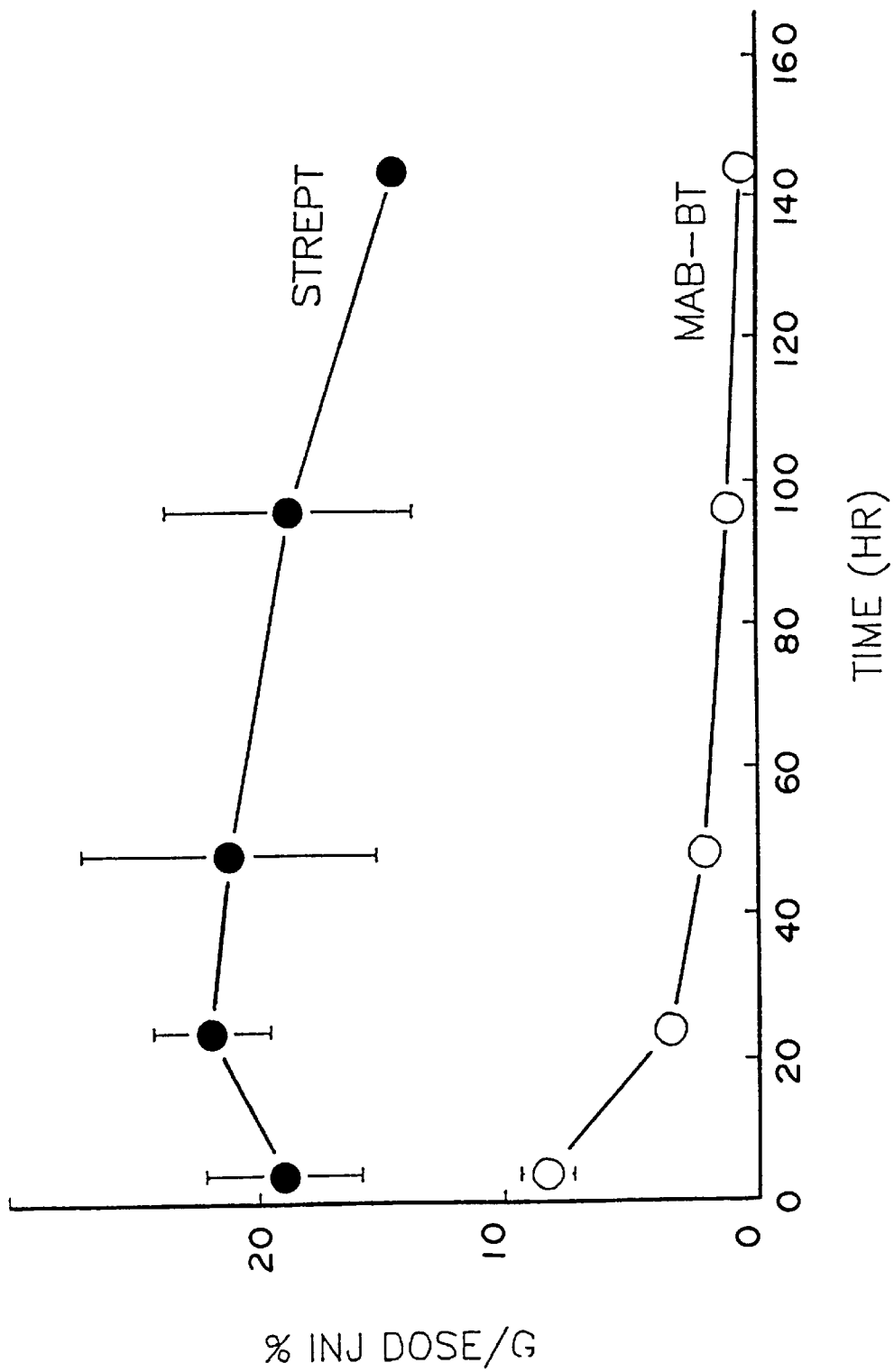
FIG. 13 depicts the prolonged liver retention of a preformed complex of NR-LU-10-biotin (○; chloramine T labeled with I-125) complexed with streptavidin (●; PIP-I-131 labeled).

A radioactivity standard of the injected doses of each complex component was also counted, and data were reduced to a percent of the total injected dose per gram of tissue. FIG. 13 shows the percent injected dose per gram of streptavidin-PIP-I-131 (STREPT) and NR-LU-10-biotin-Chloramine-T-I-125 (MAB-BT) in liver over time. The complex localized at the liver as a single molecule; however, the processing of the individual components thereof differed in the liver. The I-131-streptavidin label showed prolonged residence in the liver, while the monoclonal antibody label (I-125) was rapidly lost.

In another liver study, female nude mice xenografted with xenografted with LS-180 tumor cells, as discussed above, and were intravenously injected with 200 μg of 1:1 mol/mol NR-LU-10 monoclonal antibody covalently coupled to streptavidin, prepared as described in Example XI above. The antibody portion of the conjugate was radiolabeled with paraiodophenyl (PIP-I-125). Twenty four hours later, the mice received an injection of 0.5 μg of paraiodophenyl (PIP I-131) biocytin. Mice were sacrificed at 28, 48, 120 and 168 hours post-conjugate injection. Tissues were isolated, weighed and counted with respect to the content of each iodine radionuclide using conventional procedures therefor.

Figure 14:
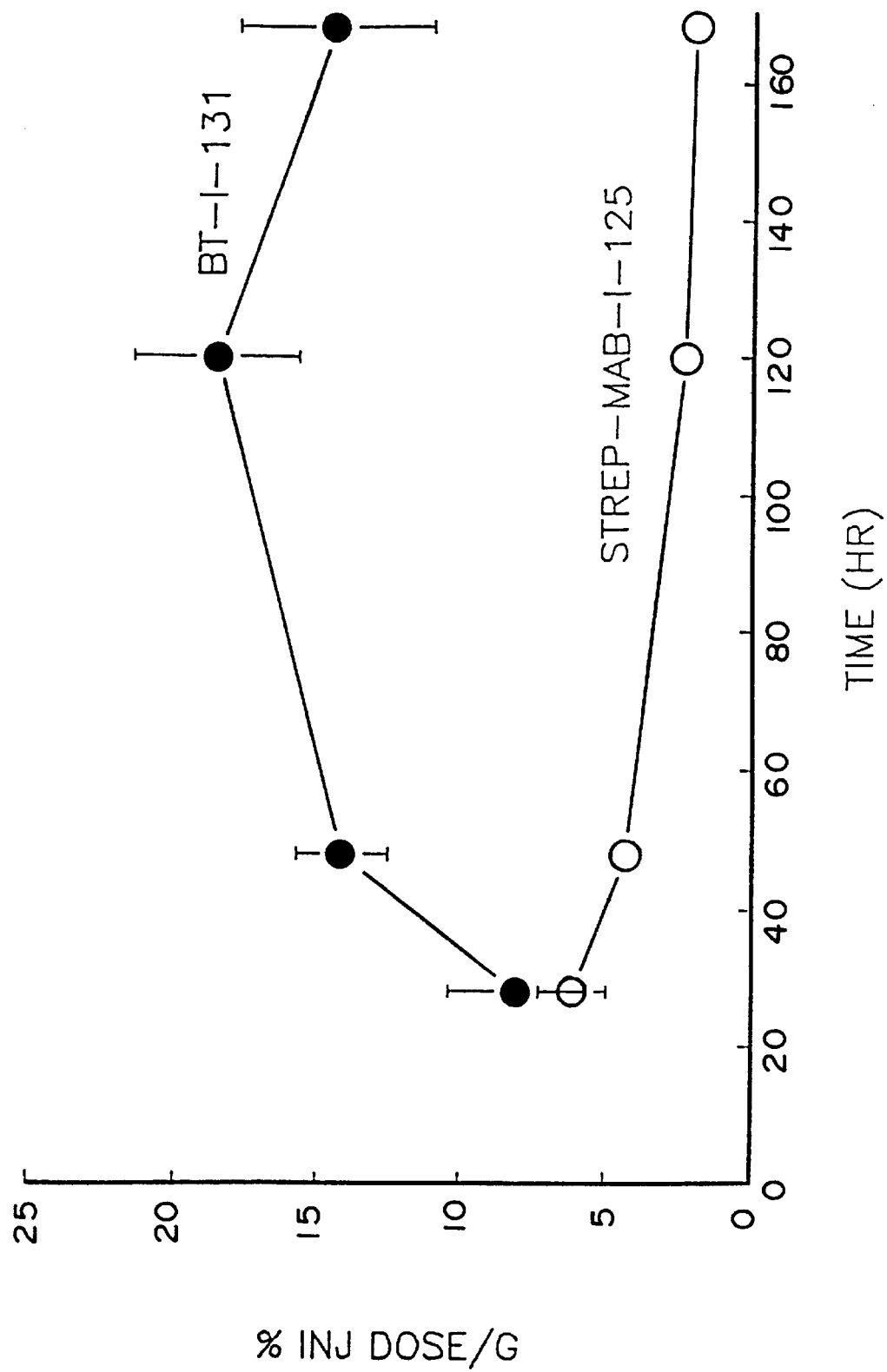
FIG. 14 depicts the prolonged liver retention of Biotin-PIP-I-131 label relative to the streptavidin-NR-LU-10-(PIP-I-125) label.

A radioactivity standard of the injected doses of each complex component was also counted, and data were reduced to a percent of the total injected dose per gram of tissue (%ID/G). FIG. 14 shows the percent injected dose per gram of streptavidin-monoclonal antibody-PIP-I-125 (STREP-MAB-I-125) and biocytin-PIP-I-131 (BT-I-131) in liver over time. When biocytin-PIP-I-131 was subsequently administered, the retention of streptavidin-bound biotin radiolabel (I-131) was prolonged relative to the retention of the antibody-bound label (I-125) on the same moiety in the liver.

EXAMPLE XVI

Tumor Uptake of PIP-Biocytin

Figure 15A:
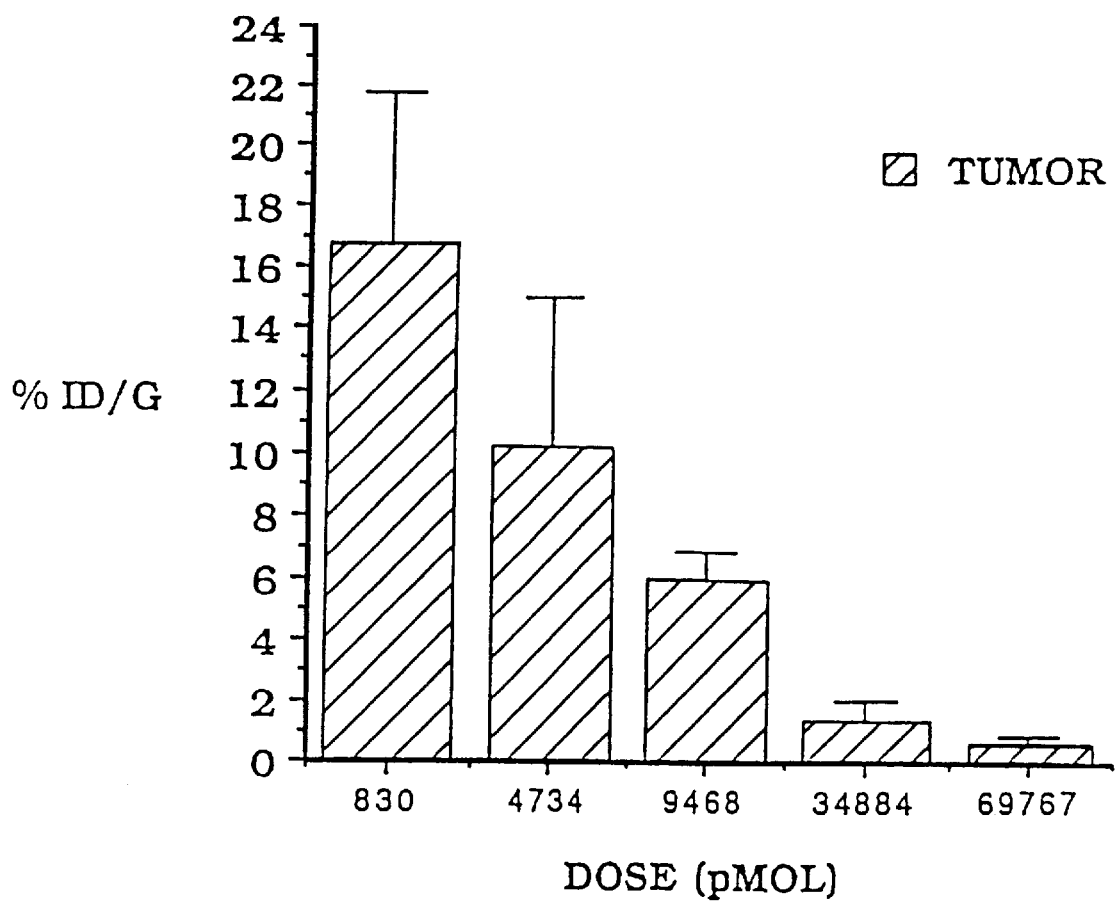
FIG. 15A depicts tumor uptake for increasing doses of PIP-Biocytin in terms of %ID/G.

PIP-Biocytin, as prepared and described in Example VII above, was tested to determine the fate thereof in vivo. The following data are based on experimentation with tumored nude mice (100 mg LS-180 tumor xenografts implanted subcutaneously 7 days prior to study) that received, at time 0, 200 μg of I-125 labeled NR-LU-10-Streptavidin conjugate (950 pmol), as discussed in Example XI above. At 24 hours, the mice received an i.v. injection of PIP-I-131-biocytin (40 μCi) and an amount of cold carrier PIP-I-127 biocytin corresponding to doses of 42 μg (69,767 pmol), 21 μg (34,884 pmol), 5.7 μg (9468 pmol), 2.85 μg (4734 pmol) or 0.5 μg (830 pmol). Tumors were excised and counted for radioactivity 4 hours after PIP-biocytin injection, and the tumor uptake data are shown in FIGS. 15A (%ID/G v. Dose) and 15B (pMOL/G v. Dose).

Figure 15B:
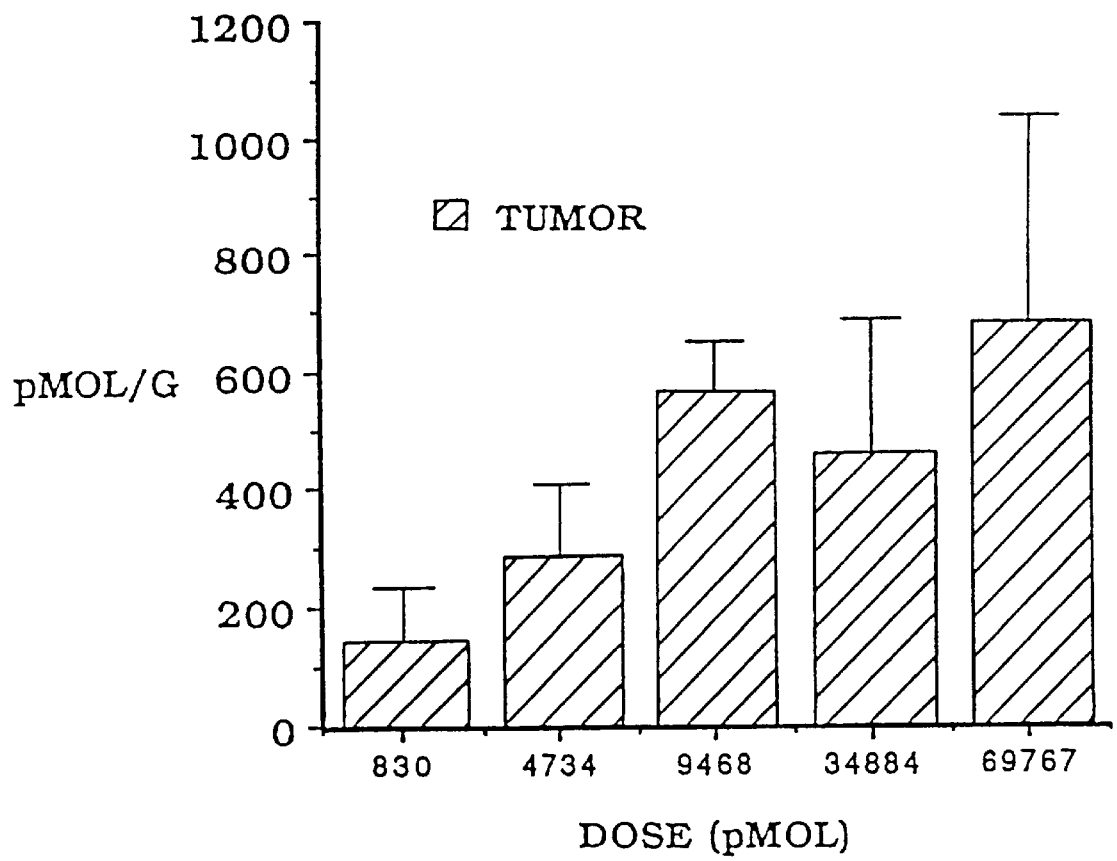
FIG. 15B depicts tumor uptake for increasing doses of PIP-Biocytin over time in terms of pMOL/G.

The three highest doses produced PIP-biocytin tumor localizations of about 600 pmol/g. Histology conducted on tissues receiving the two highest doses indicated that saturation of tumor-bound streptavidin was achieved. Equivalent tumor localization observed at the 5.7 μg dose (FIG. 15B) is indicative of streptavidin saturation as well. In contrast, the two lowest doses produced lower absolute tumor localization of PIP-biocytin, despite equivalent localization of NR-LU-10-Streptavidin conjugate (tumors in all groups averaged about 40% ID/G for the conjugate).

Figure 16A:
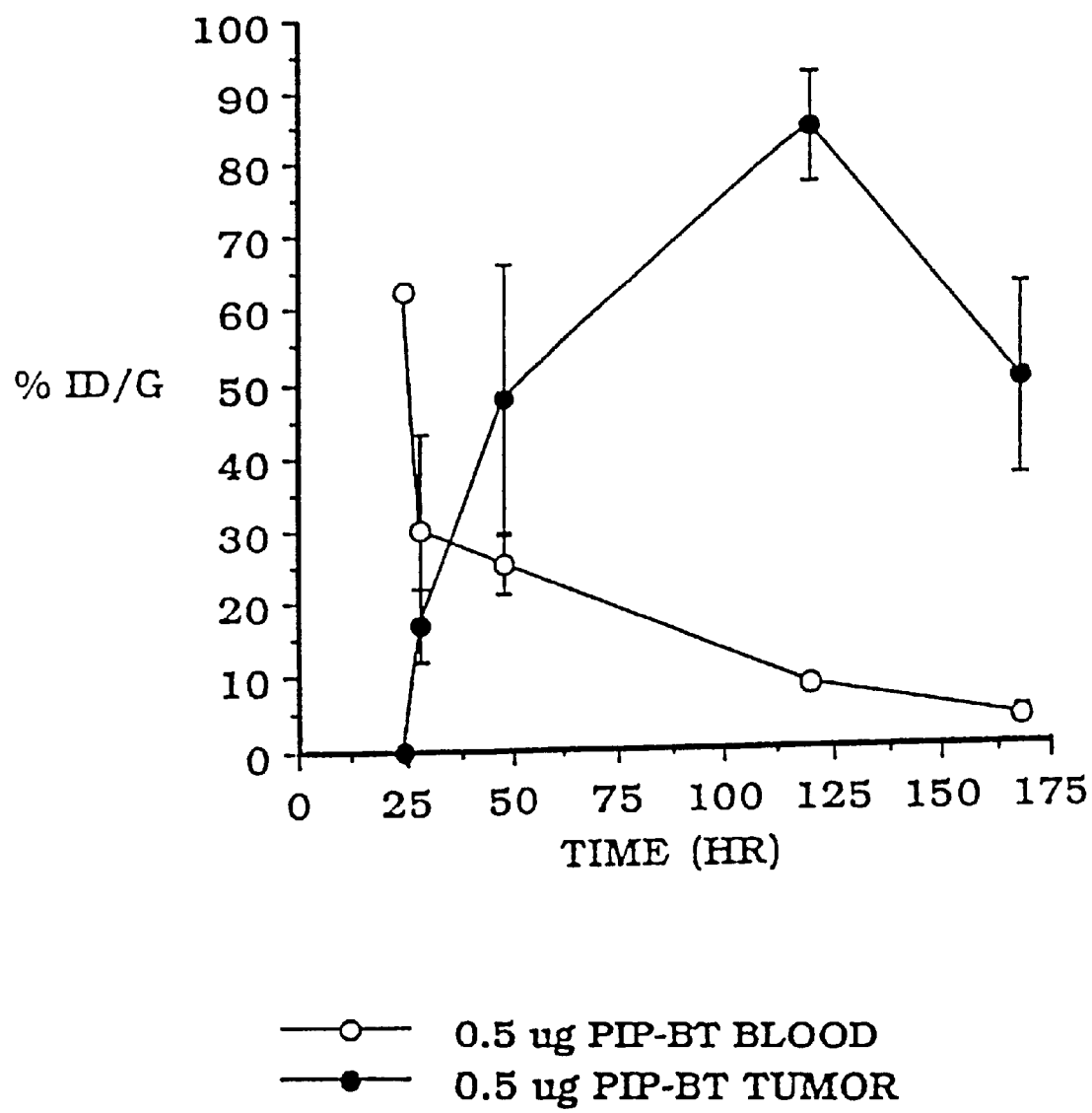
FIG. 16A depicts tumor versus blood localization of a 0.5 μg dose of PIP-Biocytin over time in terms of %ID/G.
Figure 16B:
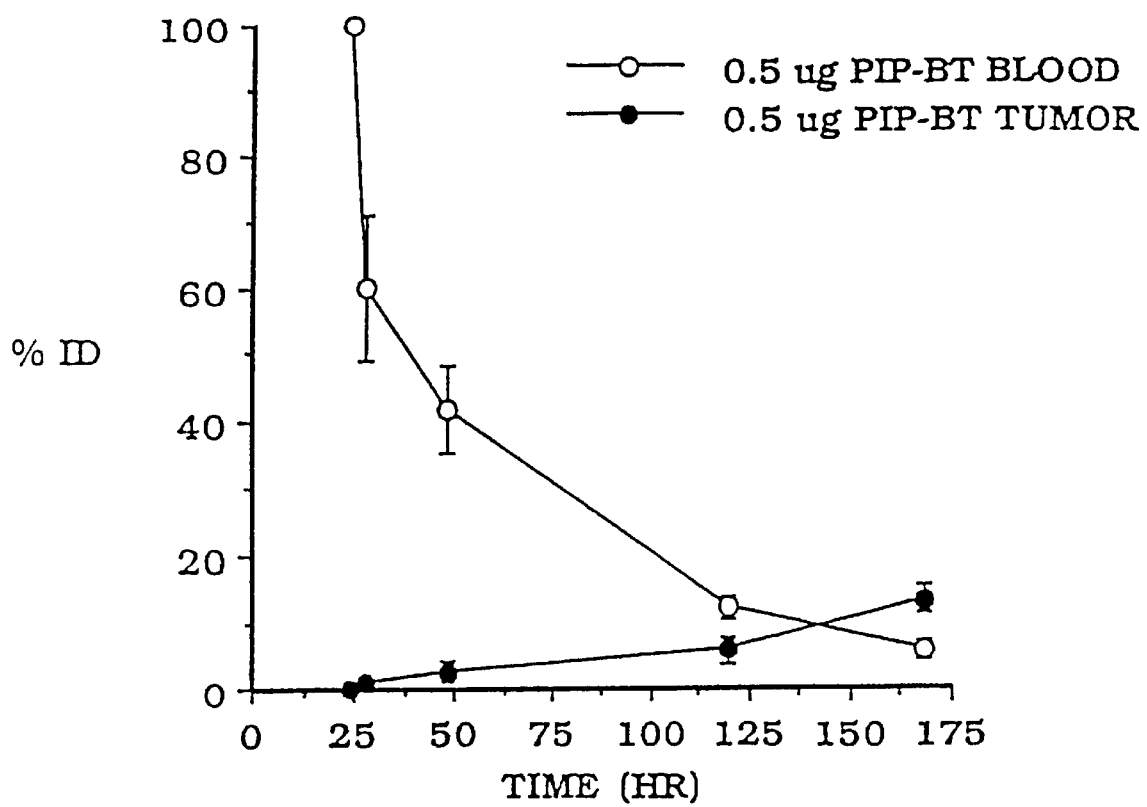
FIG. 16B depicts tumor versus blood localization of a 0.5 μg dose of PIP-Biocytin in terms of %ID.

The lowest dose group (0.5 μg) exhibited high efficiency tumor delivery of PIP-I-131-biocytin, which efficiency increased over time, as shown in FIG. 16A. A peak uptake of 85.0% ID/G was observed at the 120 hour time point (96 hours after administration of PIP-biocytin). Also, the absolute amount of PIP-biocytin, in terms of % ID, showed a continual increase in the tumor over all of the sampled time points (FIG. 16B). The decrease in uptake on a % ID/G basis (FIG. 16A) at the 168 hour time point resulted from significant growth of the tumors between the 120 and 168 hour time points.

Figure 17A:
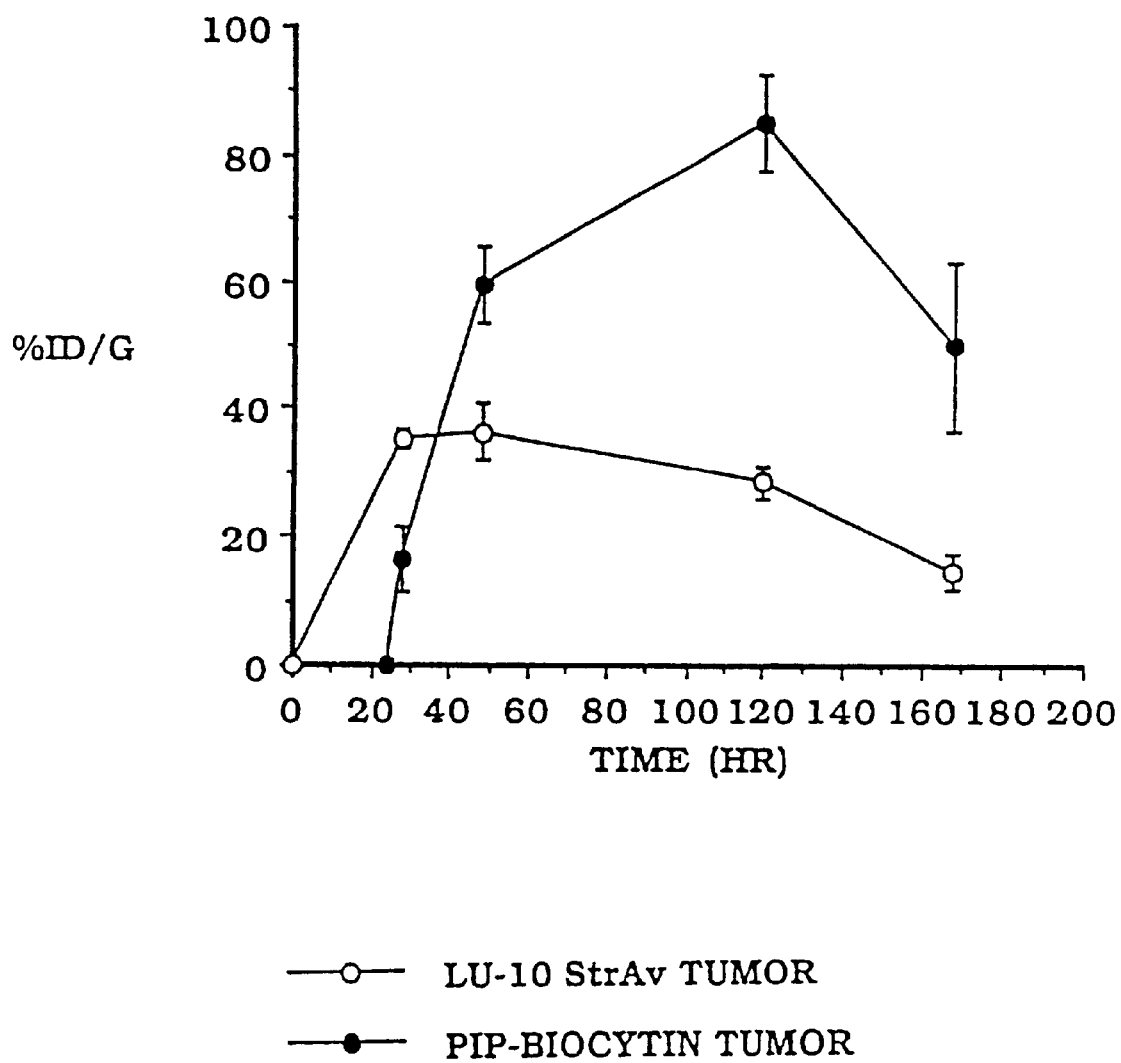
FIG. 17A depicts tumor uptake of LU-10-StrAv and PIP-Biocytin over time in terms of %ID/G.
Figure 17B:
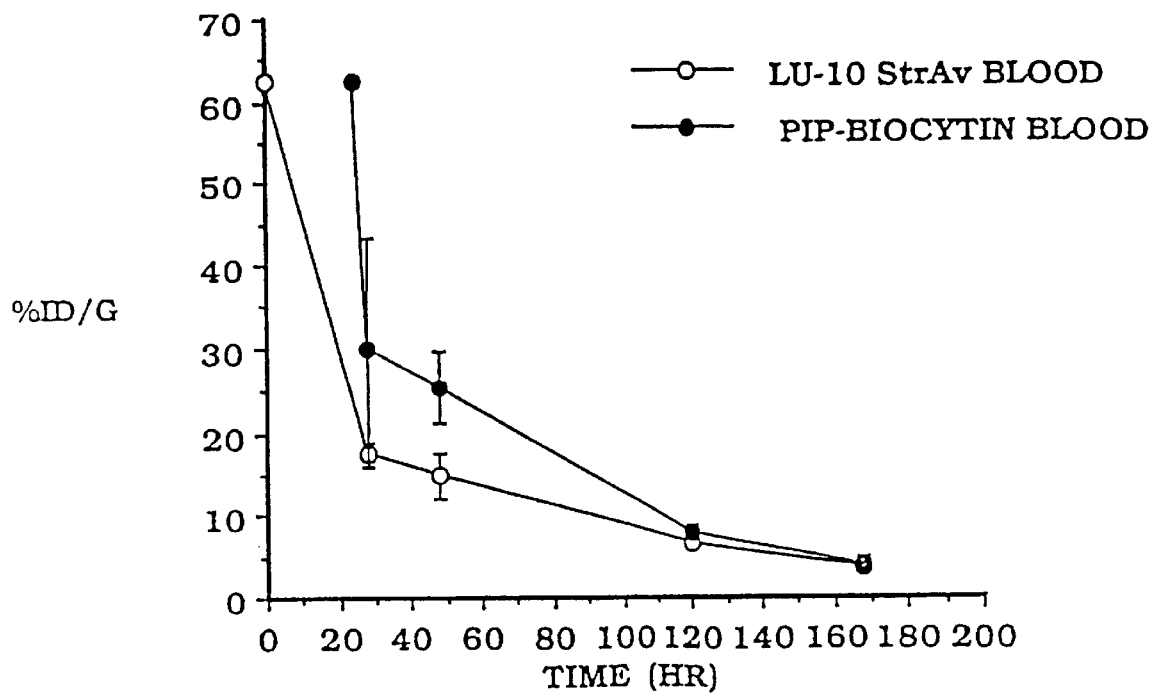
FIG. 17B depicts blood clearance of LU-10-StrAv and PIP-Biocytin over time in terms of %ID/G.

In addition, FIG. 17A shows the co-localization of NR-LU-10-Streptavidin conjugate (LU-10-StrAv) and the subsequently administered PIP-Biocytin at the same tumors over time. The localization of radioactivity at tumors by PIP-biocytin exhibited a pattern of uptake and retention that differed from that of the antibody-streptavidin conjugate (LU-10-StrAv). LU-10-StrAv exhibited a characteristic tumor uptake pattern that is equivalent to historical studies of native NR-LU-10 antibody, reaching a peak value of 40% ID/G between 24 and 48 hours after administration. In contrast, the PIP-Biodytin exhibited an initial rapid accretion in the tumor, reaching levels greater than those of LU-10-StrAv by 24-hours after PIP-Biocytin administration. Moreover, the localization of PIP-Biocytin continued to increase out to 96 hours, when the concentration of radioactivity associated with the conjugate has begun to decrease. The slightly greater amounts of circulating PIP-Biocytin compared to LU-10-StrAv at these time points (shown in FIG. 17B) appeared insufficient to account for this phenomenon.

Figure 18:
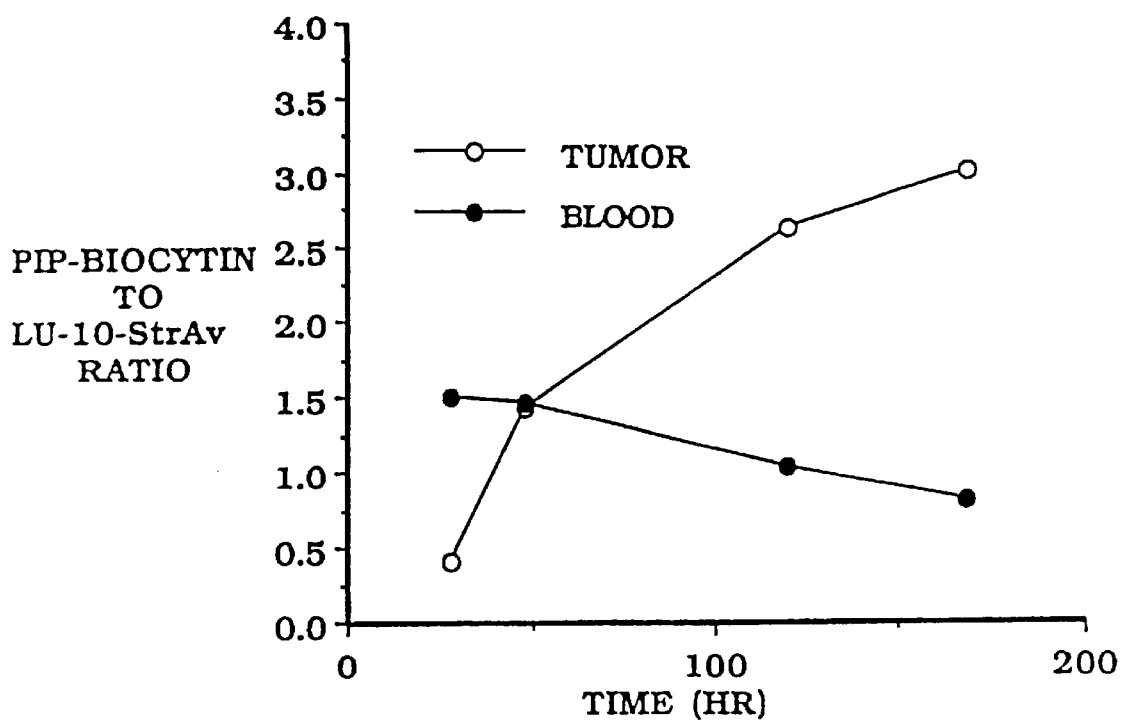
FIG. 18 depicts PIP-Biocytin:LU-10-StrAv ratio in tumor and blood over time.

As FIG. 18 clearly shows, the ratio of PIP-Biocytin to LU-10-StrAv in the tumor increased continually during the experiment, while the ratio in the blood decreased continually. This observation is consistent with a process involving continual binding of targeting moiety-containing conjugate (with PIP-Biocytin bound to it) from the blood to the tumor, with subsequent differential processing of the PIP-Biocytin and the conjugate. Since radiolabel associated with the streptavidin conjugate component (compared to radiolabel associated with the targeting moiety) has shown increased retention in organs of metabolic processing (Examples XIV and XV above), PIP-Biocytin associated with the streptavidin appears to be selectively retained by the tumor cells. Because radiolabel is retained at target cell sites, a greater accumulation of radioactivity at those sites results.

The $AUC_{tumor}/AUC_{blood}$ for PIP-Biocytin is over twice that of the conjugate (4.27 compared to 1.95, where AUC means "area under the curve"). Further, the absolute $AUC_{tumor}$ for PIP-Biocytin is nearly twice that of the conjugate (9220 compared to 4629). Consequently, an increase in radiation dose to tumor was achieved.

Kits containing one or more of the components described above are also contemplated. For instance, radiohalogenated biotin may be provided in a sterile container for use in pretargeting procedures. A chelate-biotin conjugate provided in a sterile container is suitable for radiometallation by the consumer; such kits would be particularly amenable for use in pretargeting protocols. Alternatively, radiohalogenated biotin and a chelate-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A clearing agent conjugate which comprises (i) at least one binding moiety selected from the group consisting of avidin, streptavidin, analogs and derivatives of either binding biotin with high affinity and further comprising (ii) a clearance directing moiety which is proteinaceous which comprises exposed galactose residues, at least some of which have been introduced by synthetic methods, wherein said clearing agent comprises a molecular weight ranging from about 40,000 to about 200,000 daltons and which is capable of enhancing in vivo clearance of a second conjugate from the blood via Ashwell receptor mediated clearance, wherein said second conjugate comprises the complementary binding partner of avidin or streptavidin, which is contained in the clearing agent conjugate.

2. A clearing agent conjugate which comprises (i) at least one binding moiety selected from the group consisting of avidin, streptavidin, derivatives and analogs of either binding biotin with high affinity, and further comprises (ii) a clearance directing moiety which is proteinaceous, which comprises a sufficient number of exposed galactose residues that the clearing agent provides for Ashwell receptor mediated clearance of a second conjugate which comprises biotin.

3. The clearing agent of claim 1, wherein the clearance-directing moiety is selected from the group consisting of human serum albumin, non-immunogenic serum-soluble protein, polyglutamate, polyglycine, polyarginine, and polyaspartate.

4. The clearing agent of claim 1, wherein the clearance-directing moiety is selected from the group consisting of galactose-derivatized IgM, IgG, and transferrin.

5. The clearing agent of 2, wherein the clearance-directing moiety is asialoorosomucoid, a derivative, or an analog thereof.

* * * * *